(12) United States Patent
Germain

(10) Patent No.: US 12,714,453 B2
(45) **Date of Patent: *Aug. 25, 2026**

(54) ARTHROSCOPIC DEVICES AND METHODS

(71) Applicant: Relign Corporation, Santa Clara, CA (US)

(72) Inventor: Aaron Germain, San Jose, CA (US)

(73) Assignee: Relign Corporation, Santa Clara, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 18/097,363

(22) Filed: Jan. 16, 2023

(65) Prior Publication Data

US 2023/0200832 A1 Jun. 29, 2023

Related U.S. Application Data

(63) Continuation of application No. 16/397,742, filed on Apr. 29, 2019, now Pat. No. 11,617,596.

(Continued)

(51) Int. Cl.
*A61B 17/32* (2006.01)
*A61B 17/16* (2006.01)

(52) U.S. Cl.
CPC .... *A61B 17/32002* (2013.01); *A61B 17/1637* (2013.01); *A61B 2017/320024* (2013.01)

(58) Field of Classification Search
CPC .......... A61B 17/32002; A61B 17/1637; A61B 2017/320024
See application file for complete search history.

(56) References Cited

U.S. PATENT DOCUMENTS 6,610,059 B1 8/2003 West, Jr.
8,221,404 B2 7/2012 Truckai
(Continued)

FOREIGN PATENT DOCUMENTS

CN 112367901 A 2/2021
JP 2005144142 6/2005
(Continued)

OTHER PUBLICATIONS

"U.S. Appl. No. 16/397,742, Non Final Office Action mailed Sep. 28, 2022", 10 pgs.

(Continued)

*Primary Examiner* — Sameh R Boles
(74) *Attorney, Agent, or Firm* — SCHWEGMAN LUNDBERG & WOESSNER, P.A.

(57) ABSTRACT

An arthroscopic cutting probe includes an outer sleeve having a longitudinal bore and an outer cutting window at its distal end. An inner sleeve is rotationally disposed in a bore of the outer sleeve, and the inner sleeve has a distal end, a proximal end, a longitudinal passageway, and an inner cutting window at its distal. An active electrode sleeve is disposed on an outer surface of the inner sleeve in a position opposed to the inner cutting window. Rotation of the inner sleeve relative to the outer sleeve causes the inner cutting window to rotate past the outer cutting window to resect tissue received through the cutting windows as they pass each other. Radiofrequency current can be applied to the active electrode to enhance tissue cutting then the cutting windows are being rotated or to able or cauterize tissue when the cutting windows are held stationary with the active electrode disposed through the outer cutting window.

20 Claims, 17 Drawing Sheets

Related U.S. Application Data

(60) Provisional application No. 62/664,692, filed on Apr. 30, 2018.

(56) References Cited

U.S. PATENT DOCUMENTS

| | | | |
|---|---|---|---|
| 8,323,280 | B2 | 12/2012 | Germain et al. |
| 9,204,918 | B2 | 12/2015 | Germain et al. |
| 9,247,983 | B2 | 2/2016 | Truckai et al. |
| 9,277,954 | B2 | 3/2016 | Germain et al. |
| 9,585,675 | B1 | 3/2017 | Germain et al. |
| 9,592,085 | B2 | 3/2017 | Germain et al. |
| 9,597,149 | B2 | 3/2017 | Germain et al. |
| 9,603,656 | B1 | 3/2017 | Germain et al. |
| 9,681,913 | B2 | 6/2017 | Orczy-timko et al. |
| 9,795,434 | B2 | 10/2017 | Germain et al. |
| 9,855,675 | B1 | 1/2018 | Germain et al. |
| 10,022,140 | B2 | 7/2018 | Germain et al. |
| 10,028,767 | B2 | 7/2018 | Germain et al. |
| 10,052,149 | B2 | 8/2018 | Germain et al. |
| 10,595,889 | B2 | 3/2020 | Germain et al. |
| 2001/0020167 | A1 | 9/2001 | Woloszko et al. |
| 2003/0163126 | A1 | 8/2003 | West |
| 2004/0102772 | A1 | 5/2004 | Baxter et al. |
| 2005/0027235 | A1 | 2/2005 | Knudsen et al. |
| 2013/0296847 | A1 | 11/2013 | Germain et al. |
| 2013/0331833 | A1* | 12/2013 | Bloom .............. A61B 18/1445 606/45 |
| 2014/0100567 | A1 | 4/2014 | Edwards et al. |
| 2015/0327880 | A1* | 11/2015 | Wasicek .......... A61B 17/32002 606/115 |
| 2016/0113706 | A1 | 4/2016 | Truckai et al. |
| 2016/0157916 | A1 | 6/2016 | Germain et al. |
| 2016/0346036 | A1 | 12/2016 | Orczy-Timko et al. |
| 2016/0346037 | A1 | 12/2016 | Truckai et al. |
| 2017/0128083 | A1 | 5/2017 | Germain et al. |
| 2017/0172648 | A1 | 6/2017 | Germain et al. |
| 2017/0224368 | A1* | 8/2017 | Germain ........... A61B 17/3205 |
| 2017/0252099 | A1 | 9/2017 | Orczy-Timko et al. |
| 2017/0258512 | A1 | 9/2017 | Germain et al. |
| 2017/0258519 | A1 | 9/2017 | Germain et al. |
| 2017/0290602 | A1 | 10/2017 | Germain et al. |
| 2017/0303990 | A1 | 10/2017 | Benamou et al. |
| 2018/0000534 | A1 | 1/2018 | Germain et al. |
| 2018/0008334 | A1 | 1/2018 | Germain et al. |
| 2018/0093391 | A1 | 4/2018 | Germain et al. |
| 2018/0161088 | A1 | 6/2018 | Poser et al. |
| 2018/0263649 | A1 | 9/2018 | Germain et al. |
| 2018/0303509 | A1 | 10/2018 | Germain et al. |
| 2018/0317957 | A1 | 11/2018 | Germain et al. |
| 2019/0008538 | A1 | 1/2019 | Germain et al. |
| 2019/0008541 | A1 | 1/2019 | Norton et al. |
| 2019/0015151 | A1 | 1/2019 | Germain et al. |
| 2019/0021788 | A1 | 1/2019 | Germain et al. |
| 2019/0059983 | A1 | 2/2019 | Germain et al. |
| 2019/0083121 | A1 | 3/2019 | Benamou et al. |
| 2019/0328417 | A1 | 10/2019 | Germain |

FOREIGN PATENT DOCUMENTS

| | | | |
|---|---|---|---|
| JP | 2021522884 | A | 9/2021 |
| JP | 2024045279 | | 4/2024 |
| JP | 7530833 | | 7/2024 |
| WO | WO-2013067417 | A1 | 5/2013 |
| WO | WO-2017136414 | A1 | 8/2017 |
| WO | 2017185097 | | 10/2017 |
| WO | WO-2019213090 | A1 | 11/2019 |

OTHER PUBLICATIONS

"U.S. Appl. No. 16/397,742, Notice of Allowance mailed Dec. 12, 2022", 5 pgs.

"U.S. Appl. No. 16/397,742, Response filed Sep. 14, 2022 to Restriction Requirement mailed Aug. 4, 2022", 7 pgs.

"U.S. Appl. No. 16/397,742, Response filed Nov. 18, 2022 to Non Final Office Action mailed Sep. 28, 2022", 8 pgs.

"U.S. Appl. No. 16/397,742, Restriction Requirement mailed Aug. 4, 2022", 8 pgs.

"European Application Serial No. 19797009.8, Communication Pursuant to Article 94(3) EPC filed Jun. 14, 2021", 9 pgs.

"European Application Serial No. 19797009.8, Communication Pursuant to Article 94(3) EPC mailed Aug. 26, 2022", 6 pgs.

"European Application Serial No. 19797009.8, Extended European Search Report mailed Nov. 9, 2021", 10 pgs.

"European Application Serial No. 19797009.8, Response filed Jun. 7, 2022 to Extended European Search Report mailed Nov. 9, 2021", 65 pgs.

"International Application Serial No. PCT/US2019/029927, International Preliminary Report on Patentability mailed Nov. 12, 2020", 7 pgs.

"International Application Serial No. PCT/US2019/029927, International Search Report mailed Jul. 12, 2019", 2 pgs.

"International Application Serial No. PCT/US2019/029927, Written Opinion mailed Jul. 12, 2019", 5 pgs.

Allen-Bradley, "AC Braking Basics", Web article, Rockwell Automation, Rockwell International Corporation, [Online]. Retrieved from the Internet: <http://literature.rockwellautomation.com/idc/groups/literature/documents/wp/drives-wp004_-enp.pdf>, (Feb. 2001), 4 pgs.

Allen-Bradley, "What Is Regeneration? Braking / Regeneration Manual: Regeneration Overview", Revision 1.0. Rockwell Automation, [Online]. Retrieved from the Internet: <https://www.ab.com/supportlabdrives/documentation/techpapers/RegenOverview01.pdf> Accessed Apr. 24, 2017, 6 pgs.

"European Application Serial No. 19797009.8, Response filed Mar. 7, 2025 to Communication Pursuant to Article 94(3) EPC mailed Nov. 11, 2024", 17 pgs.

"European Application Serial No. 19797009.8, Response filed Feb. 27, 2023 to Communication Pursuant to Article 94(3) EPC mailed Aug. 26, 2022", 11 pgs.

"Japanese Application Serial No. 2020-560789, Notification of Reasons for Refusal mailed Apr. 4, 2023", w English Translation, 17 pgs.

"Japanese Application Serial No. 2020-560789, Response filed Jun. 30, 2023 to Notification of Reasons for Refusal mailed Apr. 4, 2023", w English claims, 12 pgs.

"Japanese Application Serial No. 2020-560789, Examiners Decision of Final Refusal mailed Sep. 26, 2023", w English Translation, 7 pgs.

"European Application Serial No. 19797009.8, Communication Pursuant to Article 94(3) EPC filed Feb. 7, 2024", 6 pgs.

"Japanese Application Serial No. 2020-560789, Response Filed Jan. 22, 2024 to Examiners Decision of Final Refusal mailed Sep. 26, 2023", w English Claims, 15 pgs.

"European Application Serial No. 19797009.8, Communication Pursuant to Article 94(3) EPC mailed Nov. 11, 2024", 6 pgs.

"European Application Serial No. 19797009.8, Response filed Jul. 31, 2024 to Communication Pursuant to Article 94(3) EPC filed Feb. 7, 2024", 17 pgs.

* cited by examiner 200B
210

ARTHROSCOPIC DEVICES AND METHODS

CROSS-REFERENCE TO RELATED APPLICATION

The present application claims the benefit of provisional application No. 62/664,692, filed on Apr. 30, 2018, the full disclosure of which is incorporated herein by reference.

BACKGROUND OF THE INVENTION

1. Field of the Invention

This invention relates to a medical system that includes variations of motor-driven tubular cutter or arthroscopic shavers that are configured for both mechanical cutting and electrosurgical cutting, ablation and coagulation procedures.

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, some endoscopic tool systems include reusable hand piece and a selection of interchangeable tool probes having different working ends. Such working ends may each have two or more functionalities, such as soft tissue removal and hard tissue resection, so such tools systems can provide dozens of specific functionalities, providing great flexibility. While providing significant flexibility, the large variety of surgical procedures and anatomical differences require a large number of specific tool functionalities.

It is therefore an object of the present invention to provide additional interchangeable and other tool probes and methods for their use, such as improved arthroscopic tissue cutting probes and removal system wherein a motor-driven electrosurgical device is provided for selectively cutting and removing bone or soft tissue from a joint or other site. It is a further object invention to provide a single arthroscopic cutting probe or other handheld device that is capable of both mechanical and electrosurgically enhanced cutting of both soft and hard tissues. At least some of these objectives will be met by the inventions described herein.

2. Description of the Background Art

Related, commonly owned patents and published applications include: U.S. Pat. Nos. 8,221,404; 8,323,280; 9,204,918; 9,277,954; 9,247,983; 9,592,085; 9,585,675; 9,603,656; 9,681,913; 9,855,675; 10,028,767; 10,052,149; 9,795,434; and 10,022,140; and U.S. Pat. Publication Nos. US 2016-0113706; US 2016-0157916; US 2017-0128083; US 2017-0172648; US 2017-0258519; US 2017-0258512; US 2017-0290602; US 2017-0303990; US 2017-0252099; US 2018-0000534; US 2018-0161088; US 2018-0008334; US 2018-0093391; US 2019-0015151; US 2018-0263649; US 2019-0083121; US 2019-0008538; US 2018-0303509; US 2018-0317957; US 2019-0021788; US 2019-0059983; and US 2019-0008541, the full disclosures of which are incorporated herein by reference.

SUMMARY OF THE INVENTION

The present invention provides improved apparatus and methods for resecting tissue in arthroscopic and other surgical procedures. In particular, the present invention provides a single tool, typically in the form of an arthroscopic cutting probe, which can resect tissue both mechanically and with electrosurgical enhancement. The tool preferably consists of a tubular cutter with an outer sleeve and a rotating inner sleeve wherein each sleeve typically has a cutting window formed at or near a distal end thereof. An active electrode will usually be disposed on a distal exterior surface of an inner sleeve or tubular cutter so that it can apply electrosurgical current to tissue when aligned with the outer cutting window in the outer tubular sleeve. A return electrode will typically be provided along at least a portion of an exterior surface of the outer sleeve (bipolar design), although in other instances it may be provided separately from the cutting probe or other tool, typically in the form of a grounding pad placed externally on the patient's body, typically on the lower back (monopolar design).

In a first aspect of the present invention, an arthroscopic cutting probe comprises an outer sleeve having a longitudinal bore and an outer cutting window at a distal end of the outer sleeve. An inner sleeve is rotationally disposed in the longitudinal bore of the outer sleeve, and the inner sleeve has a distal end, a proximal end, a longitudinal passageway, and an inner cutting window disposed through a cylindrical wall of the inner sleeve near its distal end. Both the outer sleeve and the inner sleeve will typically comprise concentric tubular sleeves coaxially aligned along a central axis. The tubular sleeves will typically be at least partially composed of a metal or other electrically conductive material, as described in greater detail below, and will usually be connected to a proximal hub which can interface with a motor drive unit, also as discussed in greater detail below.

The arthroscopic cutting probes of the present invention will usually further comprise an active electrode disposed on an outer surface of the inner sleeve, typically near a distal end of the cylindrical wall. Rotation of the inner sleeve relative to the outer sleeve will cause the inner cutting window to rotate past the outer cutting window to resect tissue received through the cutting windows as they pass each other. The active electrode will be positioned on the inner sleeve so that the active electrode will also pass by the outer cutting window as the inner sleeve is rotated. Additionally, the active electrode can be selectively aligned within in the outer cutting window by stopping rotation of the inner sleeve at a specific rotational orientation, as described below.

In specific embodiments, the active electrode will have a curved surface that conforms to the curvature of the cylindrical wall of the inner sleeve. In specific instances, the active electrode is circumscribed by a dielectric insert, where the dielectric insert electrically isolates the active electrode from the inner sleeve, particularly metal portions of the inner sleeve which would otherwise conduct applied current. In some embodiments, an outer surface of the active electrode will be flush with a cylindrical envelope of the distal end of the inner sleeve. In other embodiments, the outer surface of the active electrode may be recessed in whole or in part within the cylindrical envelope of the distal end of the inner sleeve.

In still further specific embodiments, an aperture will be disposed through at least one of the active electrode and a region of the cylindrical wall of the inner sleeve adjacent to the active electrode. The distal end of the inner sleeve will typically be sealed except for the inner cutting window and the aperture so that a negative pressure applied to a proximal end of the longitudinal passageway in the inner sleeve can aspirate through either the inner cutting window or the aperture, depending on which is aligned with the outer cutting window. It will be appreciated that when the inner cutting window is aligned with the outer cutting window, the aperture will typically be disposed against an inner wall of the outer sleeve and blocked from aspiration. Conversely, when the aperture is exposed through the outer cutting window, at least a portion of the inner cutting window will be covered by the wall of the outer sleeve and blocked from aspiration.

In specific instances, the dielectric insert may comprise any one of a ceramic material, a glass material, a polymer, or combinations thereof. The active electrode and the dielectric insert may be disposed on a side of the cylindrical wall of the inner sleeve opposite to the inner cutting window, and the outer sleeve may comprise a metal body which can provide a return electrode to function with the active electrode.

In still further specific embodiments of the present invention, the longitudinal passageway of the inner sleeve may be configured to be coupled to a negative pressure source. In this way, aspiration through either of the inner cutting window or the aperture may be effected when the inner cutting window or the aperture is aligned with the outer cutting window.

In still other specific instances, the outer sleeve may have a bullet-shaped distal end with a spherical distal tip. The outer cutting window may be formed across the spherical distal tip. Likewise, the distal end of the inner sleeve may have a bullet-shape, with the inner cutting window formed thereacross. In this way, the inner cutting window can nest in the outer cutting window when they are in alignment. Similarly, the active electrode may nest in the outer cutting window when the active electrode is in alignment.

In a second aspect of the present invention, an arthroscopic cutting system comprises an arthroscopic cutting probe, generally as described above. The arthroscopic cutting system will further comprise at least a motor drive unit and a radio frequency (RF) power supply. The motor drive unit is configured to be coupled to the inner sleeve of the arthroscopic cutting probe in a manner which allows rotation of the inner sleeve relative to the outer sleeve. In this way, the inner and outer cutting sleeves can be caused to rotate past one another to resect tissue which is received in the cutting windows when they pass in and out of alignment. The RF power supply is configured to be coupled to the active electrode and to a return electrode which can be formed either on an exterior of the cutting probe or alternatively as a dispersive pad to be placed on the patient's skin, such as on the lower back.

The arthroscopic cutting systems of the present invention typically further comprise a controller that can be used to operate the arthroscopic cutting system in any one of at least three different modes of operation. First, the controller may be pre-programed or be programmable to activate the motor drive unit to rotate the inner cutting window past the outer cutting window while the RF power supply is not activated. In this way, the arthroscopic cutter can resect tissue in a purely mechanical manner by shearing.

In a second operational mode, the controller may be pre-programed or be programmable to cause the arthroscopic cutting probe to combine mechanical shearing with electrosurgical enhancement by delivering current from the RF power supply to the active electrode to provide enhanced cutting, ablation, or coagulation current.

In a third mode of operation, the controller may be pre-programed or be programmable to hold the motor drive stationary while delivering RF current to the active electrode. The active electrode will be exposed through the outer cutting window and can selectively deliver any one of cutting current, ablation current, or coagulation current to the tissue in the absence of mechanical shearing.

The arthroscopic cutting systems of the present invention will typically further comprise a negative pressure source which can be coupled to the longitudinal passageway of the inner sleeve to draw tissue through the cutting windows as they pass each other when operating in either of the first of second operational modes described above. The negative pressure alternatively can be applied through the aperture when the cutting system is operating in the third mode. Typically, the controller may be pre-programed or be programmable to coordinate the delivery of a negative pressure from the negative pressure source with the rotation of the inner sleeve and delivery of RF current in any one of the combinations describe herein.

In a third aspect of the present invention, a method for resecting tissue comprises providing an arthroscopic cutting probe as generally described above. The outer cutting window of the arthroscopic cutting probe is engaged against tissue, and rotation of the inner sleeve and delivery of current to the active electrode are each independently controlled to achieve any one of at least three different operational cutting and tissue treatment modes. In a first mode, the inner cutting sleeve is rotated past the outer cutting window to resect tissue received through the cutting windows as they pass each other while the outer cutting window is engaged against tissue without the delivery of RF current to the active electrode. In a second mode of operation, the cutting windows are operated as just described with the simultaneous delivery of RF current to the active electrode in order to achieve a combination of both mechanical shearing and electrosurgical treatment. In a third mode of operation, the inner sleeve is held stationary relative to the outer sleeve and RF current is delivered to the active electrode in order to achieve at least one of cutting, ablation, and tissue cauterization.

In specific aspects of the methods herein, the inner cutting window may be rotated during at least some time periods without applying RF current to the active electrode in the first mechanical resection mode. In other instances, the inner cutting window may be rotated during at least other time periods while applying RF current to the electrodes in the second electrosurgical mode of operation. In still other instances, the inner cutting window may be held stationary while applying RF current to the active electrode in the third electrosurgical mode of operation.

In yet other examples, the methods of the present invention will further apply a negative pressure to the longitudinal passageway of the inner sleeve to draw tissue through the cutting windows as they pass each other or, alternatively, apply negative pressure to the longitudinal passageway of the inner sleeve to draw tissue through the aperture while the inner sleeve remains stationary.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable band piece that carries a motor drive component. This description of the general principles of this invention is not meant to limit the inventive concepts in the appended claims.

Figure 1:
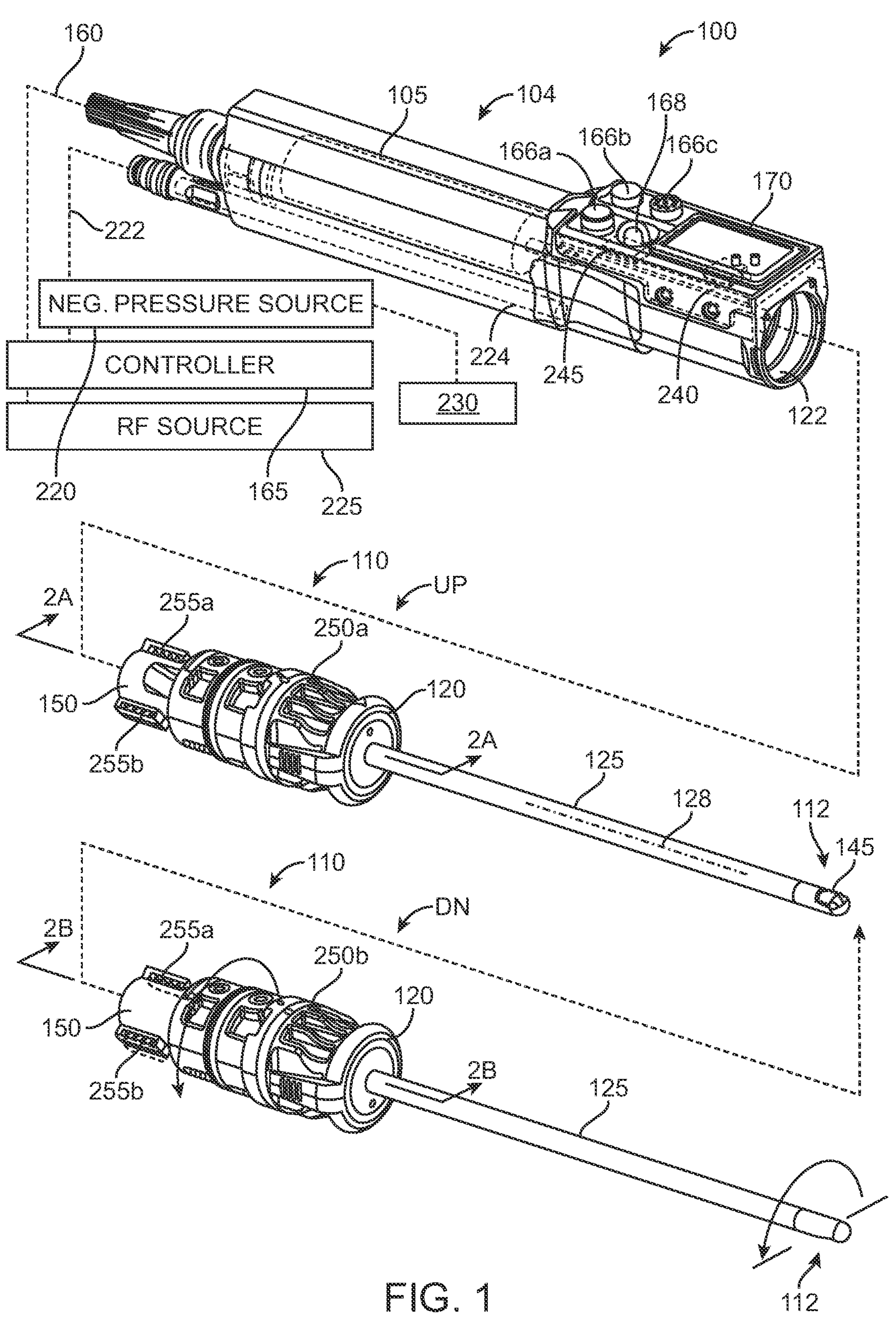
FIG. 1 is a perspective view of an arthroscopic cutting system that includes reusable hand piece with a motor drive and a detachable single-use cutting probe, wherein the cutting probe is shown in two orientations as it may be coupled to the hand piece with the probe and working end in upward orientation or a downward orientation relative to the hand piece, and wherein the hand piece includes an LCD screen for displaying operating parameters of system during use together with control actuators on the hand piece.

In one variation shown in FIG. 1, the arthroscopic system 100 of the present invention provides a hand piece 104 with motor drive 105 and a disposable shaver assembly or probe 110 with a proximal hub 120 that can be received by receiver or bore 122 in the hand piece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
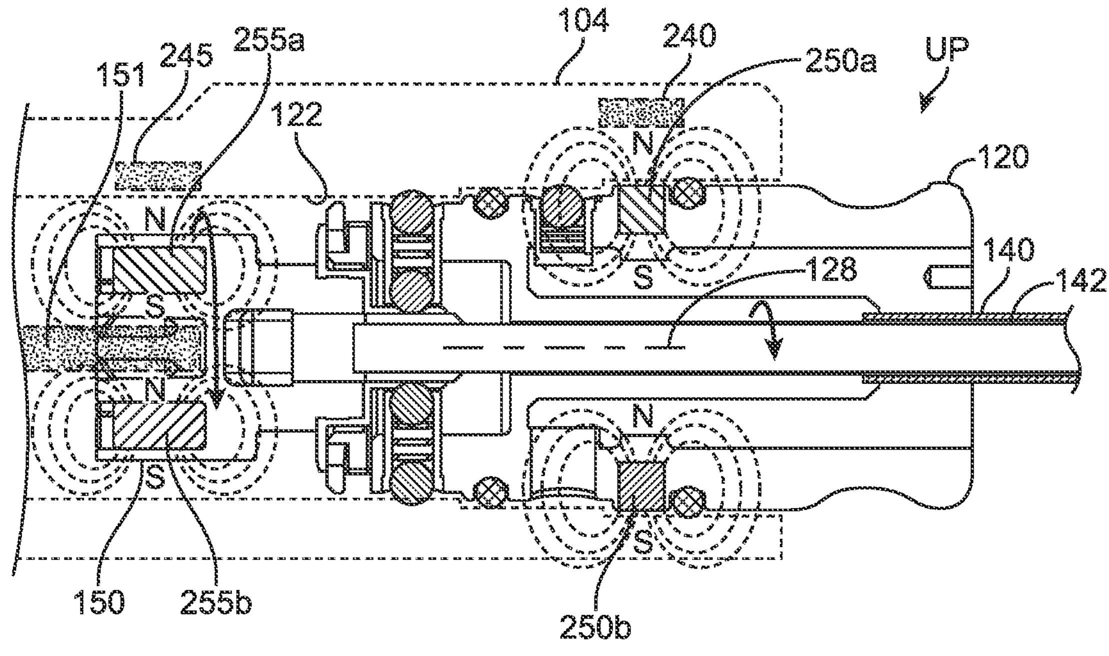
FIG. 2A is an enlarged longitudinal sectional view of the hub of the probe of FIG. 1 taken along line 2A-2A of FIG. 1 with the hub and probe in an upward orientation relative to the hand piece, further showing Hall effect sensors carried by the hand piece and a plurality of magnets carried by the probe hub for device identification, for probe orientation and determining the position of motor driven components of the probe relative to the hand piece.
Figure 3A:
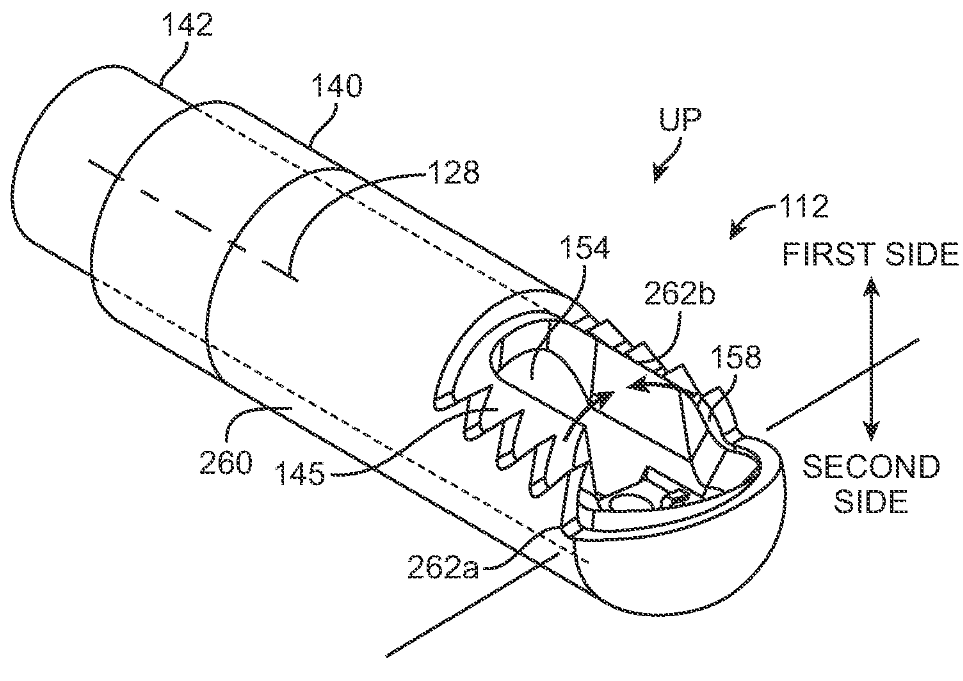
FIG. 3A is an enlarged perspective view of the working end of the probe of FIG. 1 in an upward orientation with the rotatable cutting sleeve in a first position relative to the outer sleeve wherein the window in the cutting sleeve is aligned with the window of the outer sleeve.
Figure 3B:
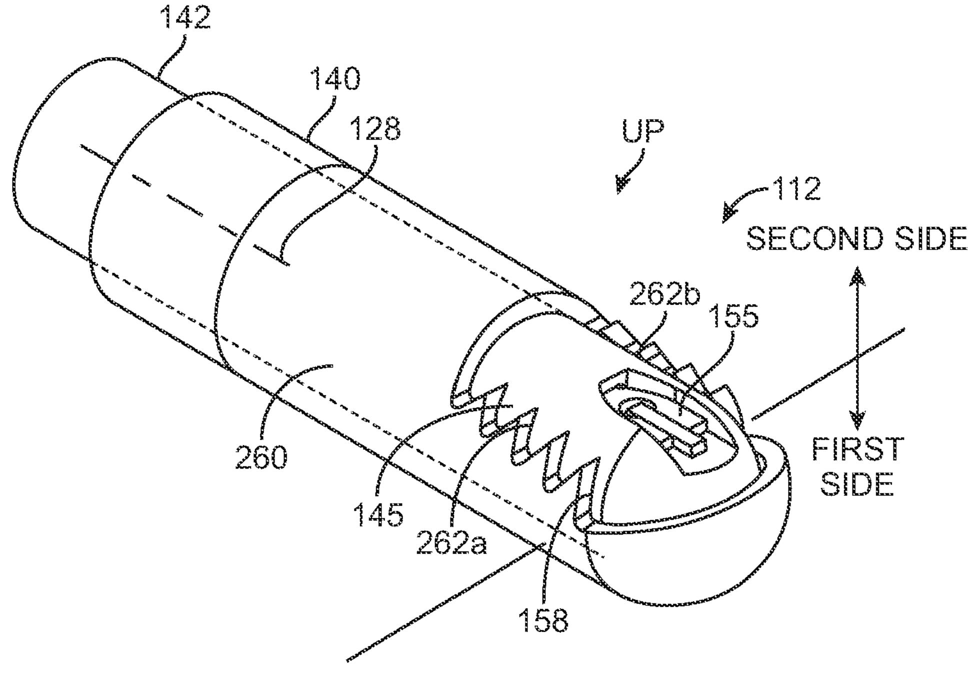
FIG. 3B is a perspective view of the working end of FIG. 1 in an upward orientation with the rotatable cutting sleeve in a second position relative to the outer sleeve wherein the electrode carried by the cutting sleeve is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting sleeve 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting sleeve 145 that is fabricated of a ceramic material with sharp cutting edges on opposing sides 152*a* and 152*b* of window 154 therein for cutting soft tissue. The motor drive 105 is operatively coupled to the ceramic cutter to rotate the cutting sleeve at speeds ranging from 1,000 rpm to 20,000 rpm. In FIG. 3B, it can be seen that cutting sleeve 145 also carries an RF electrode 155 in a surface opposing the window 154. The cutting sleeve 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the hand piece 104. More particularly, the hub 120 can be coupled to the hand piece 104 in an upward orientation indicated at UP and a downward orientation indicated at DN where the orientations are 180° opposed from one another. It can be understood that the upward and downward orientations are necessary to orient the working end 112 either upward or downward relative to the hand piece 104 to allow the physician to interface the cutting sleeve 145 with targeted tissue in all directions without having to manipulate the hand piece in 360° to access tissue.

In FIG. 1, it can be seen that the handle 104 is operatively coupled by electrical cable 160 to a controller 165 which controls the motor drive unit 105. Actuator buttons 166*a*, 166*b* or 166*c* on the handle 104 can be used to select operating modes, such as various rotational modes for the ceramic cutting sleeve 145. In one variation, a joystick 168 can be moved forward and backward to adjust the rotational speed of the ceramic cutting sleeve 145. The rotational speed of the cutter can continuously adjustable, or can be adjusted in increments up to 20,000 rpm. An LCD screen 170 is provided in the hand piece for displaying operating parameters, such as cutting sleeve RPM, mode of operation, etc.

Figures 4, 5:
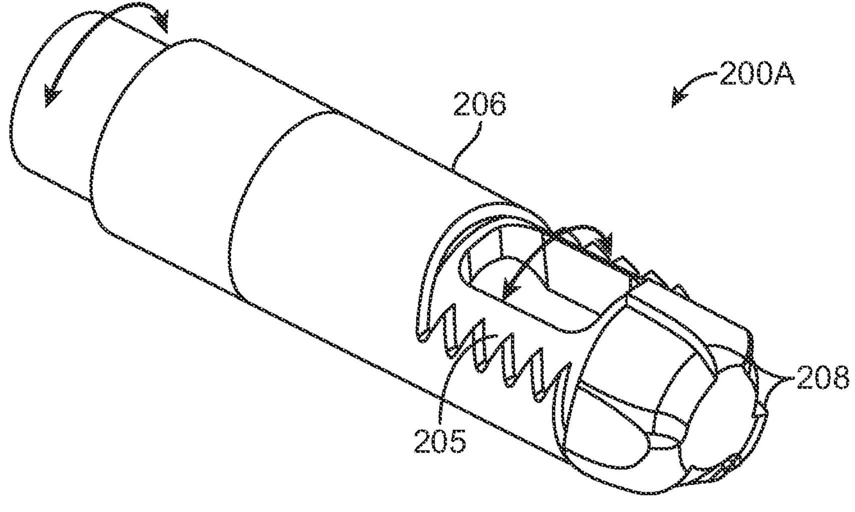
FIG. 4 is a perspective view of a working end of a variation of a probe that may be detachably coupled to the hand piece of FIG. 1, wherein the working end includes a bone burr extending distally from the outer sleeve.
FIG. 5 is a perspective view of a working end of a variation of a probe that may be detachably coupled to the hand piece of FIG. 1, wherein the working end has a reciprocating electrode.
Figure 6:
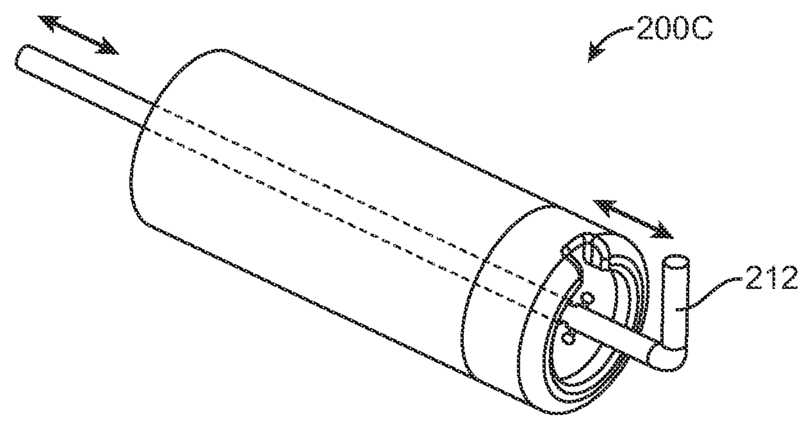
FIG. 6 is a perspective view of a working end of another variation of a probe that may be detachably coupled to the hand piece of FIG. 1, wherein the working end has a hook electrode that has extended and non-extended positions.
Figure 7:
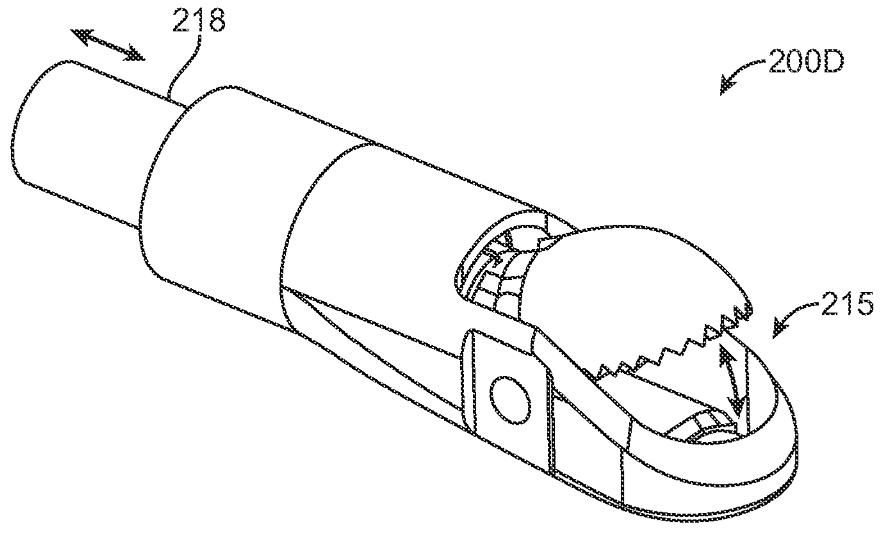
FIG. 7 is a perspective view of a working end of yet another variation of a probe that may be detachably coupled to the hand piece of FIG. 1, wherein the working end has an openable-closeable jaw structure for cutting tissue.

It can be understood from FIG. 1 that the system 100 and hand piece 104 is adapted for use with various disposable probes which can be designed for various different functions and procedures. For example, FIG. 4 illustrates a different variation of a probe working end 200A that is similar to working end 112 of probe 110 of FIGS. 3A-3B, except the ceramic cutting sleeve 205 extends distally from the outer sleeve 206 and the cutting sleeve has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating sleeve 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same hand piece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in hand piece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and hand piece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to hand piece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the hand piece 104 in an upward or downward orientation relative to the hand piece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
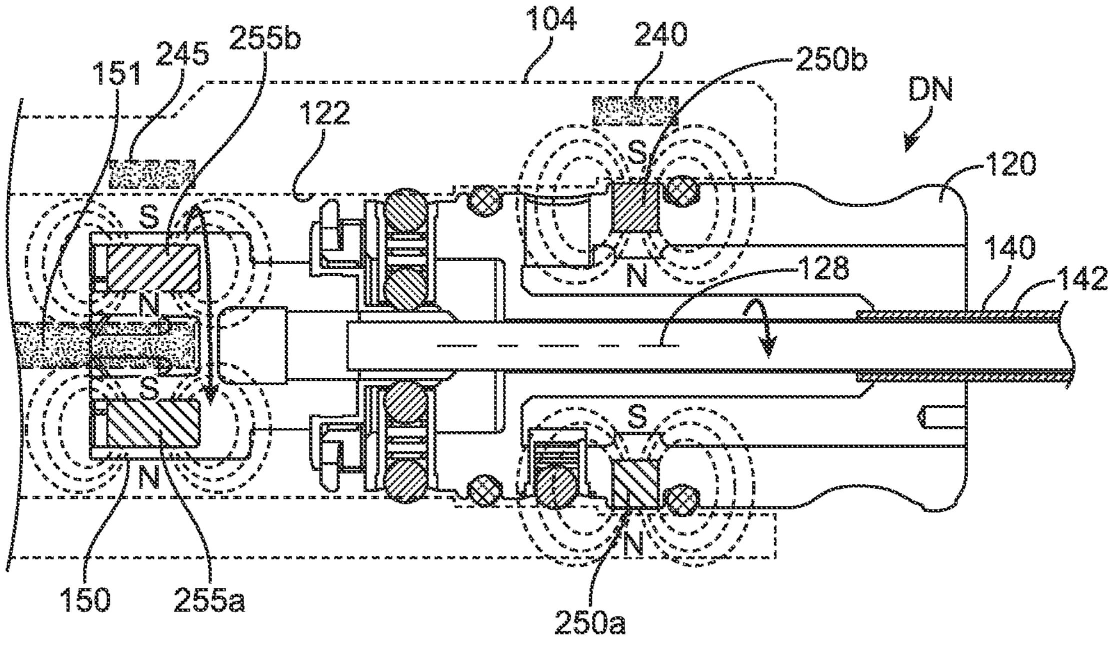
FIG. 2B is a sectional view of the hub of FIG. 1 taken along line 2B-2B of FIG. 1 with the hub and probe in a downward orientation relative to the hand piece showing the Hall effect sensor and magnets having a different orientation compared to that of FIG. 2A.

Referring to FIGS. 1 and 2A-2B, it can be seen that hand piece 104 carries a first Hall effect sensor 240 in a distal region of the hand piece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The hand piece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the hand piece, (ii) the upward or downward orientation of the probe hub 120 relative to the hand piece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250*a* and 250*b* in a surface portion thereof. The Hall sensor 240 in hand piece 104 is in axial alignment with either magnet 250*a* or 250*b* when the probe hub 120 is coupled to hand piece 104 in an upward orientation (FIGS. 1 and 2A) or a downward orientation (FIGS. 1 and 2B). In one aspect as outlined above, the combination of the magnets 250*a* and 250*b* and the Hall sensor 240 can be used to identify the probe type. For example, a product portfolio may have from 2 to 10 or more types of probes, such as depicted in FIGS. 1 and 4-7, and each such probe type can carry magnets 250*a*, 250*b* having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to hand piece 104 in upward and downward orientations, in which the North (N) and South(S) poles of the magnets 250*a*, 250*b* are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250*a* and 250*b* with their different orientations of North (N) and South(S) poles relative to central longitudinal axis 128 of hub 120 are also used to identify the upward orientation UP or the downward orientation DN of hub 120 and working end 112. In use, as described above, the physician may couple the probe 110 to the hand piece receiving passageway 122 with the working end 112 facing upward or downward based on his or her preference and the targeted tissue. It can be understood that controller algorithms adapted to stop rotation of the cutting sleeve 145 in the window 158 of the outer sleeve 104 of working end 112 need to "learn" whether the working end is facing upward or downward, because the orientation or the rotating cutting sleeve 145 relative to the hand piece and Hall sensor 240 would vary by 180°. The Hall sensor 240 together with a controller algorithm can determine the orientation UP or the downward orientation DN by sensing whether the North (N) or South(S) pole of either magnet 250*a* or 250*b* is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating sleeve or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255*a* or 255*b* with the North (N) and South(S) poles of magnets 255*a* or 255*b* being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255*a*, 255*b*). Thereafter, a controller tachometer algorithm using a clock can determine and optionally display the RPM of the drive coupling 150 and, for example, the cutting sleeve 145 of FIG. 3A.

In another aspect of the invention, the Hall sensor 245 and magnets 255*a* and 255*b* (FIGS. 1 and 2A) are used in a set of controller algorithms to stop the rotation of a motor-driven component of a working end, for example, cutting sleeve 145 of FIGS. 1 and 3A-3B in a pre-selected rotational position. In FIG. 3A, it can be seen that the inner sleeve 142 and a "first side" of cutting sleeve 145 and window 154 therein is stopped and positioned in the center of window 158 of outer sleeve 140. The stationary position of cutting sleeve 145 and window 154 in FIG. 3A may be used for irrigation or flushing of a working space to allow for maximum fluid outflow through the probe.

FIG. 3B depicts inner sleeve 142 and a "second side" of cutting sleeve 145 positioned about the centerline of window 158 in the outer sleeve 140. The stationary or stopped position of cutting sleeve 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting sleeve 145 and electrode 155 were rotated so as to be close to an edge 262*a* or 262*b* of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting sleeve 145 and electrode 155 can be determined. A controller algorithm can further calculate the rotational angle of the electrode 155 away from the centerline default position as the Hall sensor 245 can sense lessening of magnetic field strength as a magnet 255*a* or 255*b* in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255*a* or 255*b* drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on hand piece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting sleeve 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255*a* and 255*b* are attached to inner sleeve 142 and cutting sleeve 145 in a pre-determined angular relationship relative to longitudinal axis 128 so that the Hall sensor generates signals responsive to magnets 255*a*, 255*b* is the same for all probes within a probe type to thus allow the controller algorithm to function properly.

Figure 8:
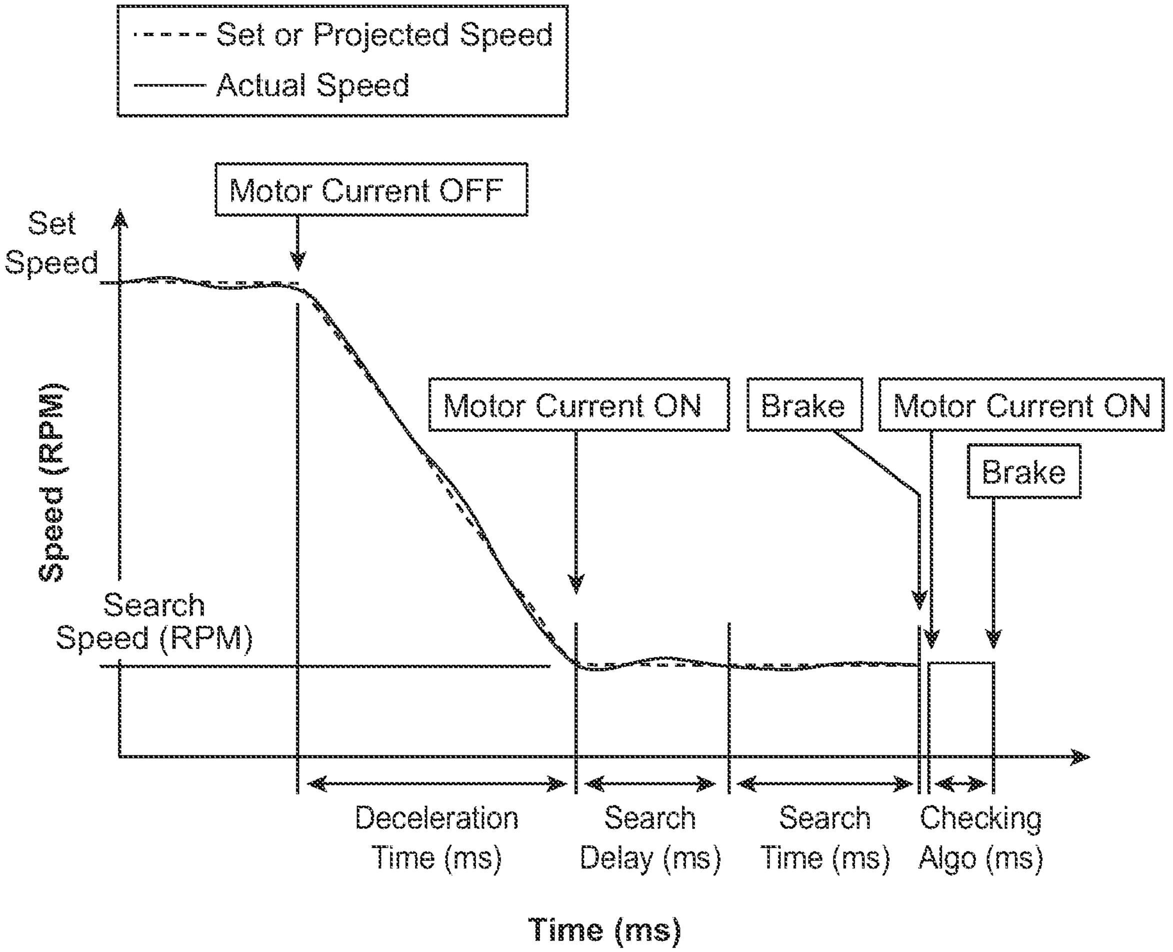
FIG. 8 is a chart relating to set speeds for a probe with a rotating cutting sleeve as in FIGS. 1 and 3A that schematically shows the method used by a controller algorithm for stopping rotation of the cutting sleeve in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting sleeve 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting sleeve 145 and electrode 155 within at the centerline position or within 0° to 5° of the targeted centerline default position. Dynamic braking is described further below. FIG. 8 schematically illustrates various aspects of controller algorithms for controlling the rotational speed of the cutting sleeve and for stopping the cutting sleeve 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting sleeve 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255*a* or 255*b* in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting sleeve 145, and also depending on whether the physician has completely disengaged the cutting sleeve from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255*a* and 255*b* as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255*a* and 255*b* which may vary from the specified strength. After a new single-use probe 110 (FIG. 1) is coupled to the hand piece 104, and after actuation of the motor drive 105, the positioning algorithm will rotate the drive coupling at least 180° and more often at least 360° while the Hall sensor 245 quantifies the field strength of the particular probe's magnets 255*a* and 255*b*. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a hand piece with a motor drive, a controller, and a probe with a proximal hub configured for detachable coupling to the hand piece, wherein the motor drive is configured to couple to a rotating drive coupling in the hub and wherein the drive coupling carries first and second magnets with North and South poles positioned differently relative to said axis, and coupling the hub to the hand piece, activating the motor drive to thereby rotate the drive coupling and magnets at least 180°, using a hand piece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting sleeve 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
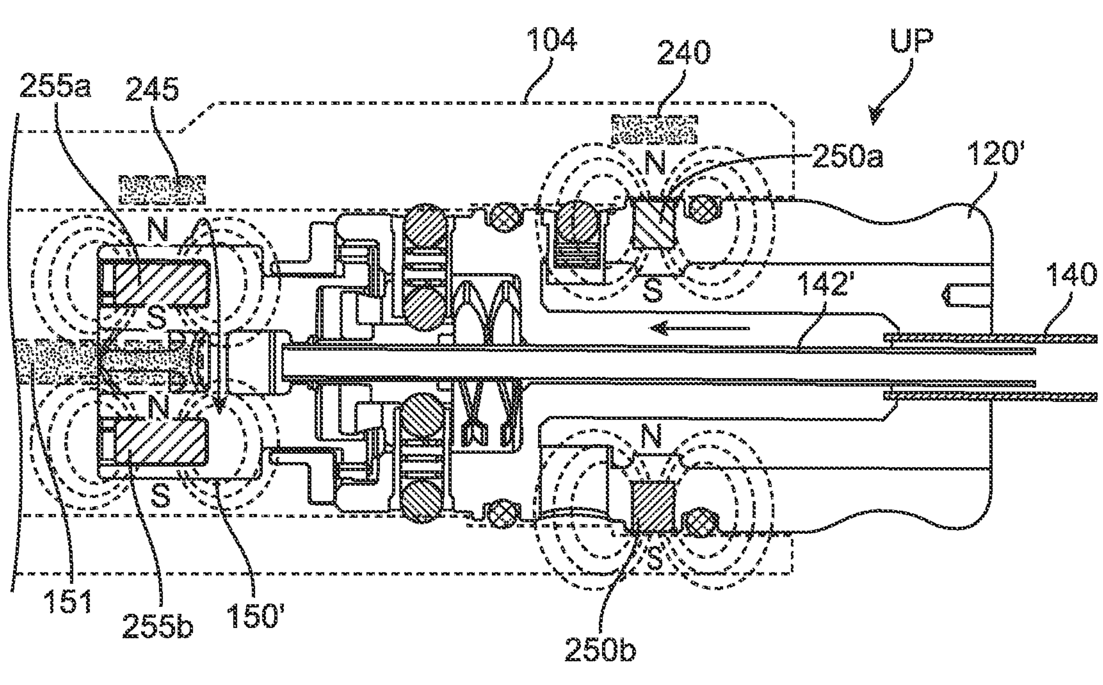
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the hand piece.
Figure 9B:
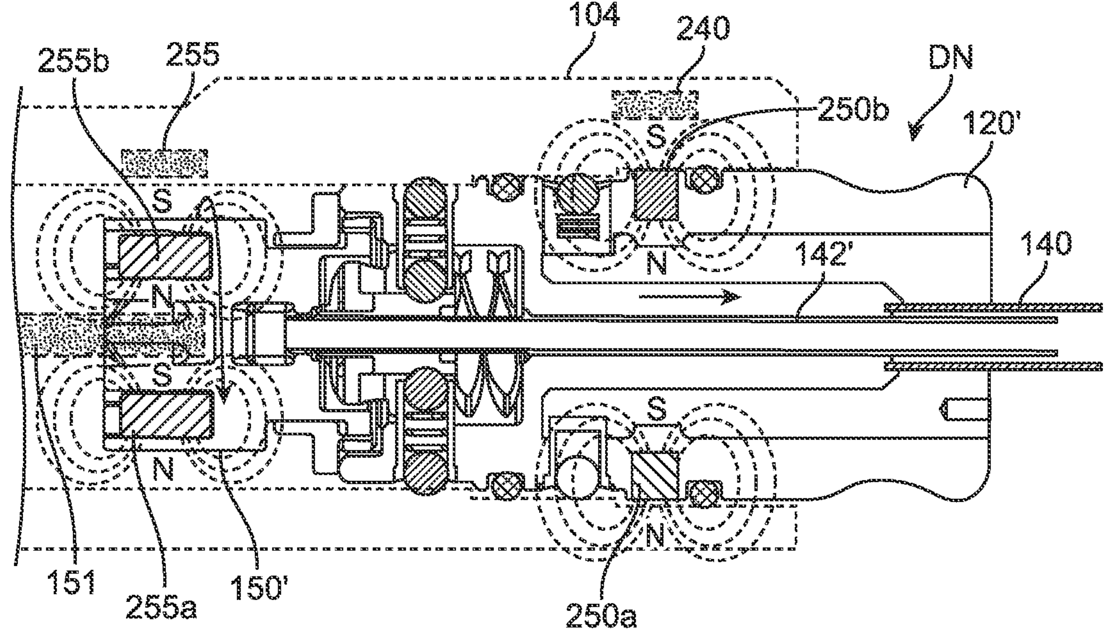
FIG. 9B is a sectional view of the hub of FIG. 9A rotated 180° in a downward facing position relative to the hand piece.

FIGS. 9A-9B are longitudinal sectional views of a probe hub 120' that corresponds to the working end 200B of FIG. 5 which has a reciprocating electrode 210. In FIGS. 9A-9B, the hand piece 104 and Hall affect sensors 240 and 245 are of course the same as described above as there is no change in the hand piece 104 for different types of probes. The probe hub 120' of FIGS. 9A-9B is very similar to the hub 120 of FIGS. 2A-2B with the first and second identification/orientation magnets 250*a* and 250*b* being the same. The third and fourth rotation al position magnets 255*a* and 255*b* also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Now turning to FIGS. 10 and 11A-11C, another variation of an arthroscopic shaver or resection probe 400 is shown which somewhat similar to that of FIGS. 1 and 3A-3B which comprises a tubular cutter having a proximal hub 402 coupled to an elongated shaft assembly 405. The shaft assembly comprises an outer sleeve 410 and a concentric inner sleeve 415 that extends along axis 418 to a working end 420. The hub 402 again is adapted for coupling to a hand piece and motor drive operated by a controller and controller algorithms having the features as described in previous embodiments for rotating the inner sleeve 415 as well as stopping the inner sleeve 415 in a selected rotational position, such as a window-closed or window-open position. The working end 420 again has an outer sleeve window 422 that cooperates with an inner sleeve window 425 for engaging and resecting tissue.

The variation in FIGS. 10 and 11A-11C, the shaft assembly 405 differs in that the outer sleeve 410 has a distal end portion that comprises a dielectric body or housing 440 in which the outer window 422 is disposed. In one variation, the proximal 426*a* and medial portions 426*b* of the outer sleeve 410 that extend from the hub 402 comprise a thin wall, electrically conductive metal tube 428, such as a stainless steel. As will be described further below, a proximal or medial portion of the metal tube functions as an electrode indicated at 430 in FIG. 10. In a typical variation, the dielectric housing 440 comprises a ceramic material, a glass material, a polymeric material or a combination thereof. In some variations, the dielectric housing 440 can be carried within a metal support portion 442 of the metal outer tube 428 which extends underneath or partly surrounding the dielectric housing 440.

Figure 11A:
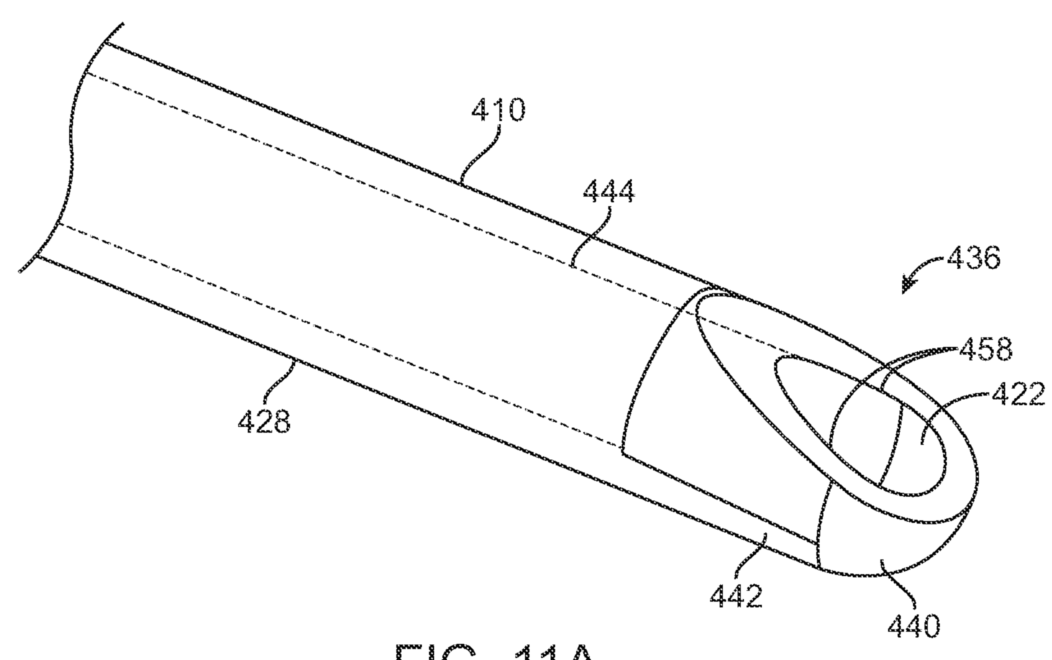
FIG. 11A is perspective view of the working end of the outer sleeve of the probe of FIG. 10 separated from the inner sleeve.

FIG. 11A shows the working end 436 of the outer sleeve 410 with outer window 422 separated from the inner sleeve 415. It can be seen that passageway or bore 444 extends through the outer sleeve 410 and the dielectric housing 440 in which the concentric inner sleeve 415 is rotationally disposed.

Figure 11B:
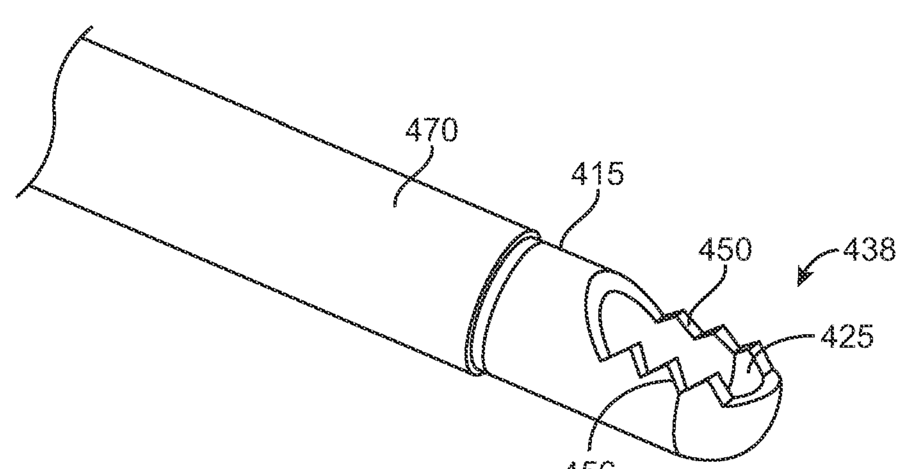
FIG. 11B is perspective view of the working end of the inner sleeve of the probe of FIG. 10 with the inner sleeve window facing upward.
Figure 11C:
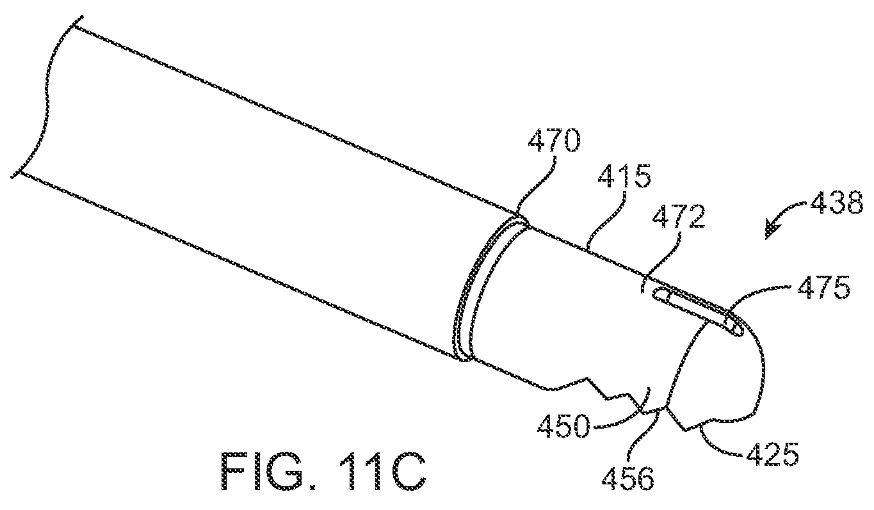
FIG. 11C is perspective view of the working end of the inner sleeve of FIG. 11B with the inner sleeve window facing downward.

FIG. 11B shows the working end 438 of the inner sleeve 415 separated from the outer sleeve 410 of FIG. 11A in a first position in which the inner sleeve window 425 is facing upwardly. FIG. 11C illustrates the same inner sleeve 415 rotated 180° so that the inner sleeve window 425 is facing downward. As can be seen in FIGS. 11B-11C, the inner sleeve 415 comprises a thin wall metal tube of a conductive material, such as stainless steel, which then can function as an electrode indicated at 450. Thus, the working end 438 of the inner sleeve 415 which carries the inner window 425 comprises electrode 450 which is configured with a close rotational fit in the bore 444 of the dielectric housing 440 so that the inner window edges 456, with optional teeth, and the edges 458 outer sleeve window and act like scissors for shearing or resecting tissue, either mechanically or electrosurgically, as will be described further below. Still referring to FIGS. 11A and 11B, the inner sleeve 415 is a thin layer 470 of an insulating polymer such as a heat shrink tubing or the parylene coating to electrically insulate the outer surface of inner sleeve 415 from the inner surface of the metal outer sleeve 428.

Figure 10:
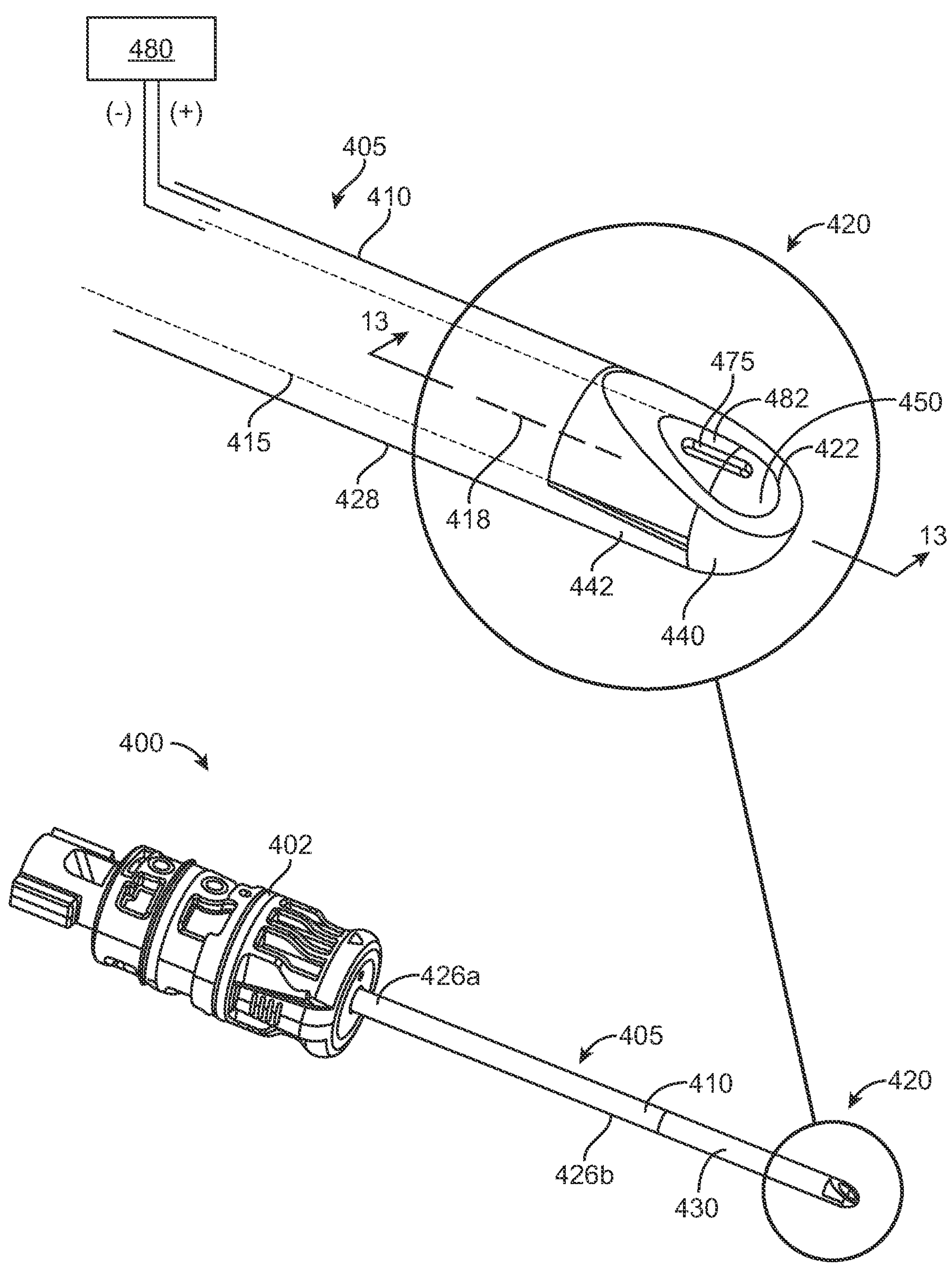
FIG. 10 is a perspective view of another variation of a probe that shows a motor-driven, rotating inner cutting sleeve that comprises an electrode and outer sleeve carrying a distal dielectric housing.

In another aspect of the invention as can be seen in FIGS. 10 and 11C, the back side 472 of the inner sleeve 415 opposing the inner sleeve window 425 has at least one opening 475 that is provided for fluid outflows therethrough when the inner sleeve 415 is rotated relative to the outer sleeve 410 to a window-closed position (see FIG. 1).

Figure 12:
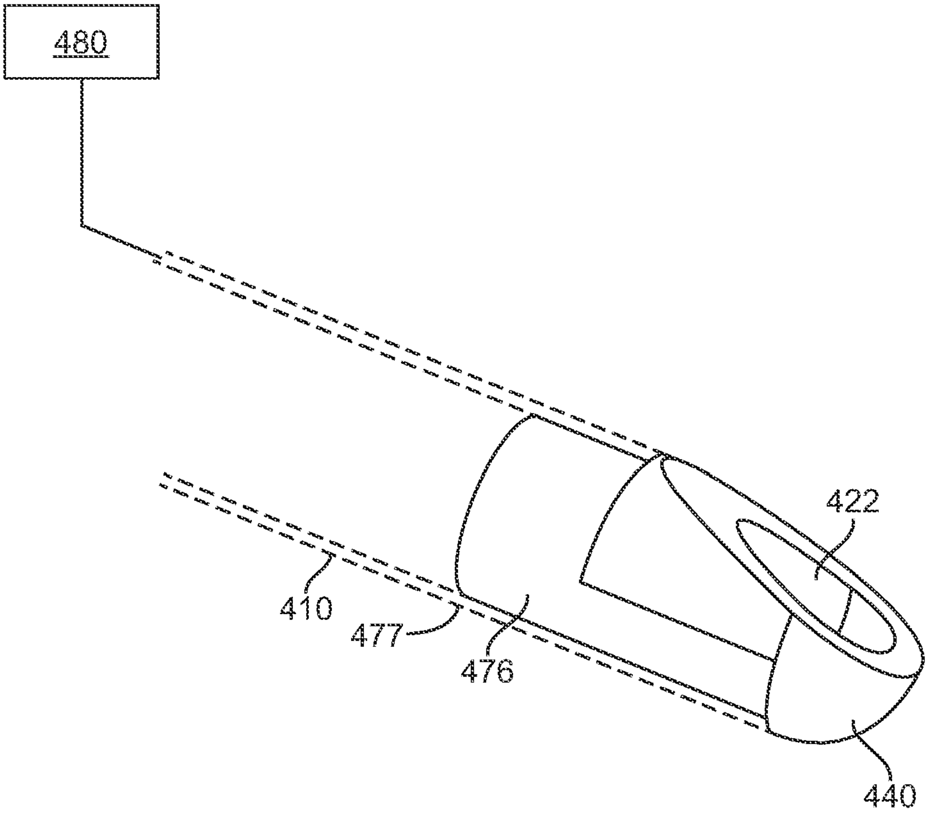
FIG. 12 is perspective view of the dielectric housing of FIG. 11A.

FIG. 12 illustrates the dielectric or ceramic housing 440 with the outer sleeve 415 in phantom view. It can be seen that the dielectric housing 440 has a recessed portion 476 in which the distal end 477 of outer sleeve 410 surrounds and supports the dielectric housing 440. The thickness of the wall of the dielectric housing around the window 422 can range from about 0.05" to 0.20".

Figure 13:
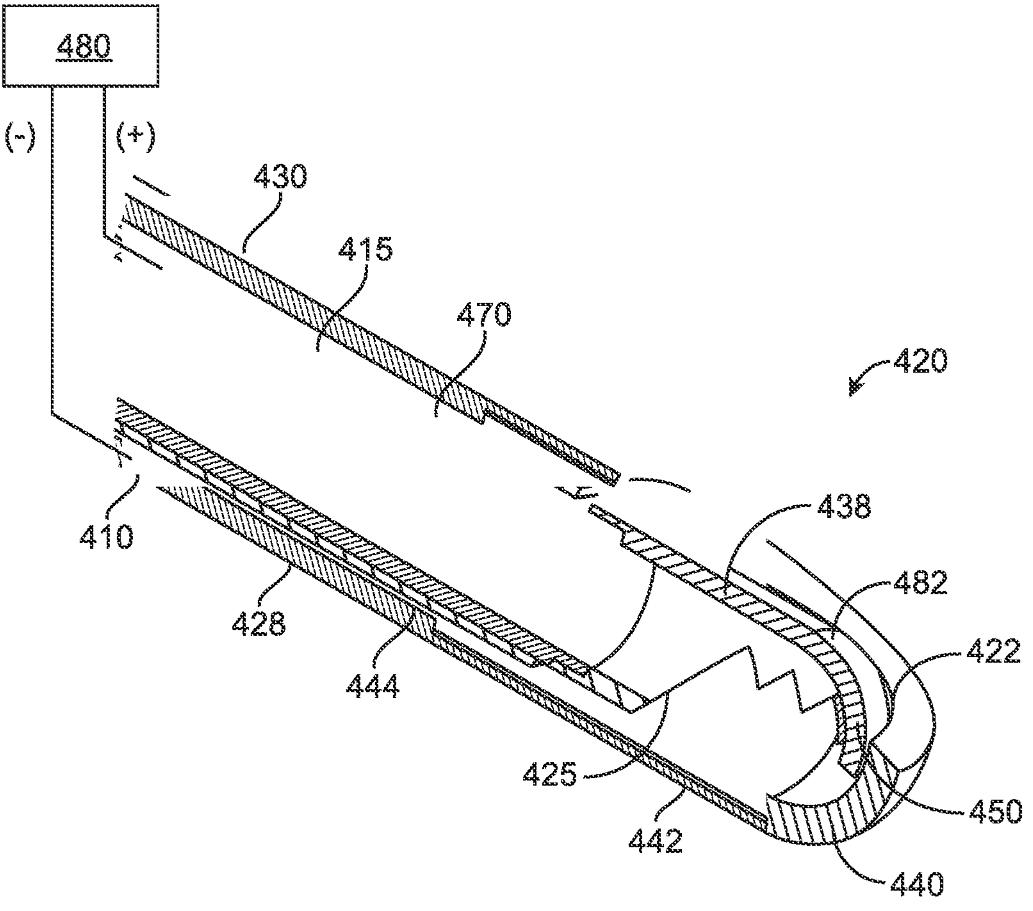
FIG. 13 is a sectional view of the working end of FIG. 10 taken along line 13-13 of FIG. 10.

FIG. 13 is a longitudinal sectional view of the working end 420 of the probe of FIGS. 10-11C which shows the working end 420 window-closed position. It can be seen that the working end 438 of the inner sleeve 415 is in close tolerance with bore 444 in outer sleeve and dielectric housing 440 so that rotation of inner sleeve 415 can shear tissue engaged by the inner sleeve and outer sleeve windows 422, 425. FIG. 13 further illustrates the support portion 442 of the metal outer sleeve 428 that extends underneath the ceramic housing 440. In addition, FIG. 13 also shows the thin insulating layer 470 that surrounds the inner sleeve 415 to electrically insulate the inner sleeve from the metal outer sleeve 428.

Still referring to FIG. 13, an RF source 480 is coupled to both the inner sleeve 410 and the outer sleeve 415 to provide for electrosurgical functionality. The RF source 480 is capable of delivering an average of at least 100 W, or at least 200 W, or at least 300 W or at least 400 W to allow for ignition of a plasma over the exposed outward or exterior surface 482 of the inner sleeve 415 in the window-closed position as shown in FIG. 10. Typically, the outward surface 482 of the inner sleeve 415 in the window-closed position is less than 15 $mm^2$, less than 10 $mm^2$ or less than 8 $mm^2$. In operation, it can be thus understood that rotation of the inner sleeve 415 in the outer sleeve 410 in a first mode of operation can mechanically shear tissue engaged by the windows 422 and 425 or in a second mode of operation to electrosurgically resect tissue. That is, the inner sleeve can rotate and shear tissue contemporaneously the RF source 480 delivers the cutting current to the inner sleeve to energize the edges of the inner sleeve window 425 which can create a plasma to shear tissue, or to assist in shearing tissue.

In general, a resecting probe or treatment device corresponding to the invention comprises shaft assembly 405 having an outer sleeve 410 and a rotatable inner sleeve 415 co-axially received in a bore 444 in outer sleeve, wherein the inner and outer sleeves have respective inner and outer cutting windows, 422 and 425, with cooperating cutting edges in distal portions thereof, and wherein the distal portion of the outer sleeve that carries the cutting window 422 comprises a dielectric housing 440 and the distal working end 438 of the inner sleeve 415 that carries the inner cutting window 425 comprises an RF electrode 450.

In this variation, the dielectric material of the dielectric housing can comprises at least one of a ceramic, a glass and a polymer. For example, the ceramic material can be selected from the group consisting of alumina, zirconia, silicon nitride, yttria-stabilized zirconia, magnesia-stabilized zirconia, ceria-stabilized zirconia and zirconia toughened alumina.

The probe of FIG. 10 further comprises a motor configured to selectively rotate in the inner sleeve in first and second rotational directions, with the radiofrequency (RF) source 480 coupled to the electrode. Further, a controller is operatively coupled to the motor and to the RF source.

In general, the controller includes an algorithm for stopping the motor to position the inner sleeve in a window-closed position or a window-open position. Further, the controller is configured to selectively operate in (i) a first mode in which the motor rotates or oscillates the inner sleeve with the RF electrode not energized for mechanically cutting tissue; (ii) a second mode in which the motor rotates or oscillates the inner sleeve with the RF electrode energized for electrosurgically cutting tissue; (iii) a third mode in which the inner sleeve is stationary in the window-closed position and the RF electrode is energized for applying coagulative or ablative energy to tissue; and (iv) a fourth mode in which the inner sleeve is stationary in the window-open position and the RF electrode is energized for applying coagulative or ablative energy to tissue.

Figure 14:
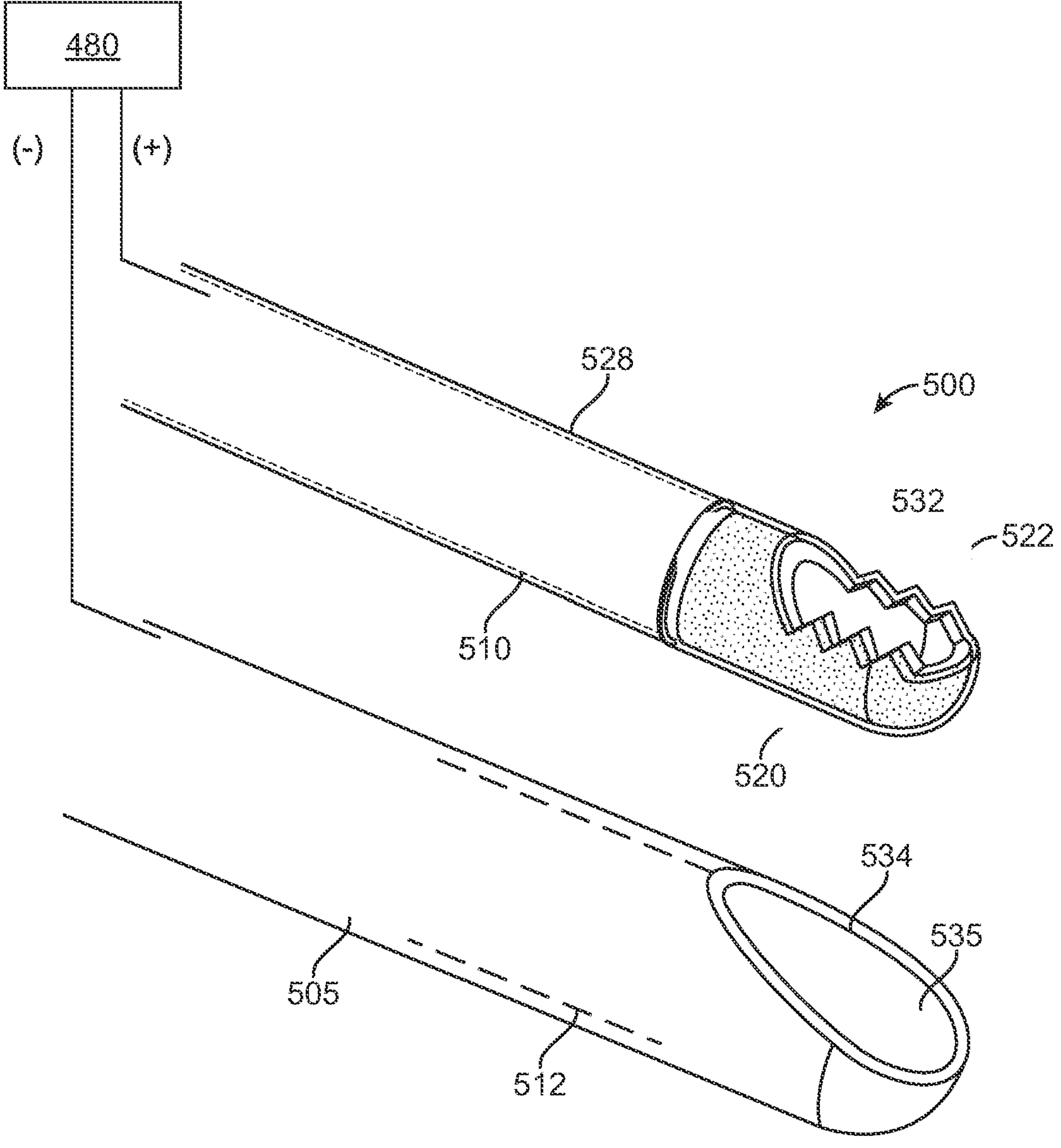
FIG. 14 is a perspective view of another variation of a probe that shows a motor-driven, rotating inner cutting sleeve that comprises an electrode with an insulative coating that rotates in a metal outer sleeve.

FIG. 14 illustrates another variation of a working end 500 that includes an outer sleeve 505 and inner sleeve 510 that is adapted to rotate in bore 512 of the outer sleeve. In this variation, the outer sleeve 505 comprises a conductive metal tube without the ceramic housing as in the previous variation of FIGS. 10 and 11A. In this variation, the dielectric component that separates the conductive inner sleeve 510 from the conductive outer sleeve comprises a dielectric coating or layer 520 on the distal end 522 of the inner sleeve 510 and the polymer coating 528 over the proximal and medial portions of the inner sleeve 510. The dielectric material 520 at the distal end 522 of the inner sleeve can be a ceramic or a glass material that can be configured with sharp edges 532 so as to provide a sharp, durable cutting edges 532 for cooperating with the edges 534 of the outer sleeve window 535. In all other respects, the variation of FIG. 14 can operate is the same manner as the variation described above in FIGS. 10-13.

Figure 15:
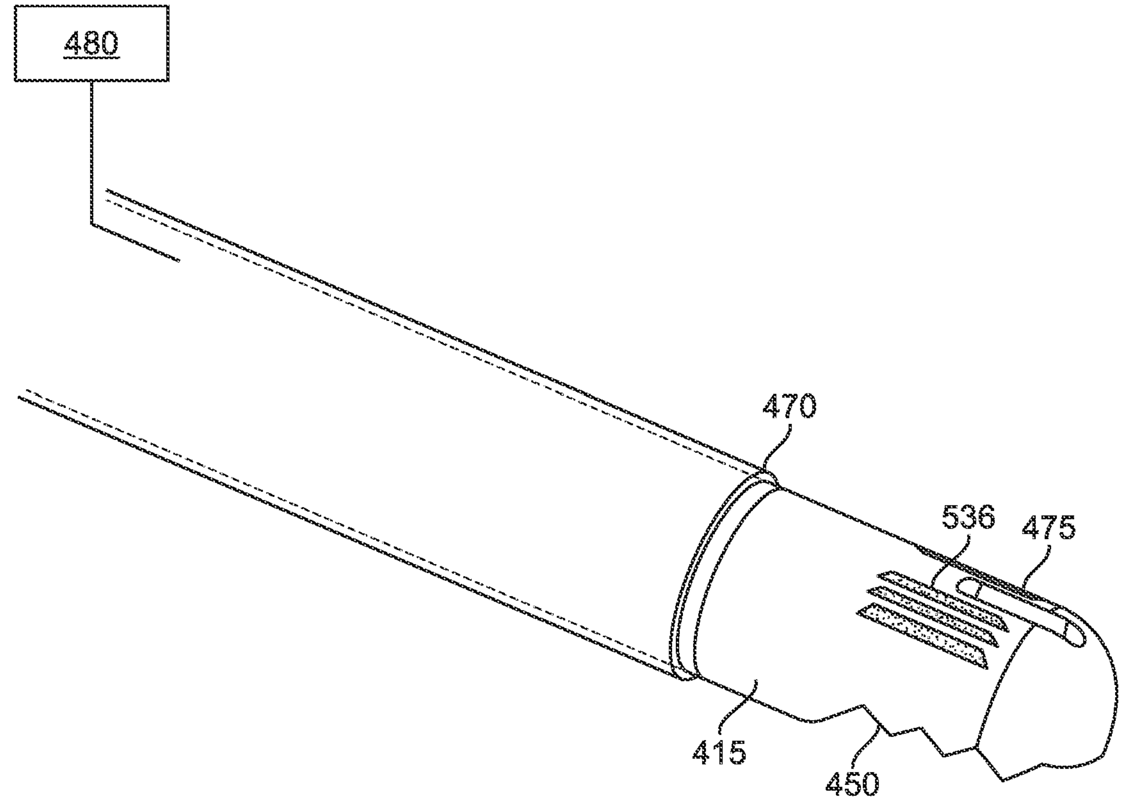
FIG. 15 is a perspective view of a working end of a motor-driven, rotating inner sleeve similar to that of FIGS. 11B-11C with abrasive cutting features for abrading bone.

FIG. 15 is a perspective view of a working end of a motor-driven, rotating inner sleeve similar to that of FIGS. 11B-11C with abrasive cutting features or sharp edges 536 for abrading bone. Thus, another mode of operation can be to rotate the inner sleeve at high speeds to use the abrasive features 536 to cut or abrade bone, typically without RF current being applied to the electrode surface. In some methods, and RF current can be applied to the electrode surface while abrading hard tissue or cauterizing purposes.

Figure 16:
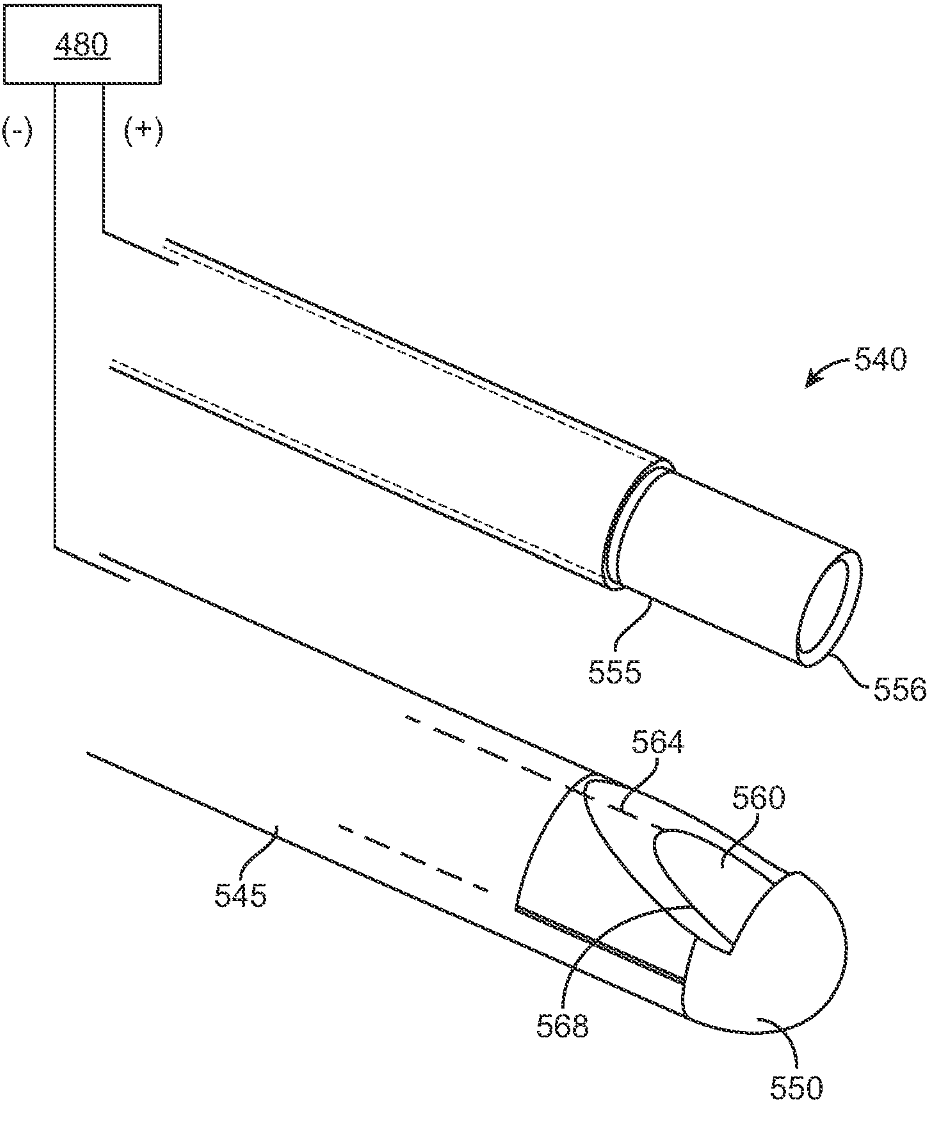
FIG. 16 is a perspective view of a working end of another variation of a probe that shows a motor-driven, reciprocating inner sleeve comprising an electrode that reciprocates in a dielectric housing carried by the outer sleeve.

FIG. 16 illustrates another variation of working end 540 that operates under similar principles to that of the variation of FIG. 10 wherein the outer sleeve 545 carries a distal dielectric or ceramic housing 550 and a concentric inner sleeve 555 with cutting edges 556 is adapted to move relative to the outer sleeve window 560 in the dielectric housing 550. However, in this variation, the inner sleeve 555 is adapted to reciprocate rather than rotate. In other respects, the cutting edges 556 of the inner sleeve 555 are configured with a close fit to the bore 564 in the dielectric housing 550 such that the inner sleeve cutting edges 556 and the edges 568 of outer sleeve window 560 shear tissue engaged by the window 560. As described in previous embodiments, an RF source 480 is operatively coupled to both the inner and outer sleeves 545 and 555 to allow for electrosurgical cutting. In use, the reciprocation of inner sleeve thus can resect tissue mechanically or electrosurgically as described above.

Figure 17:
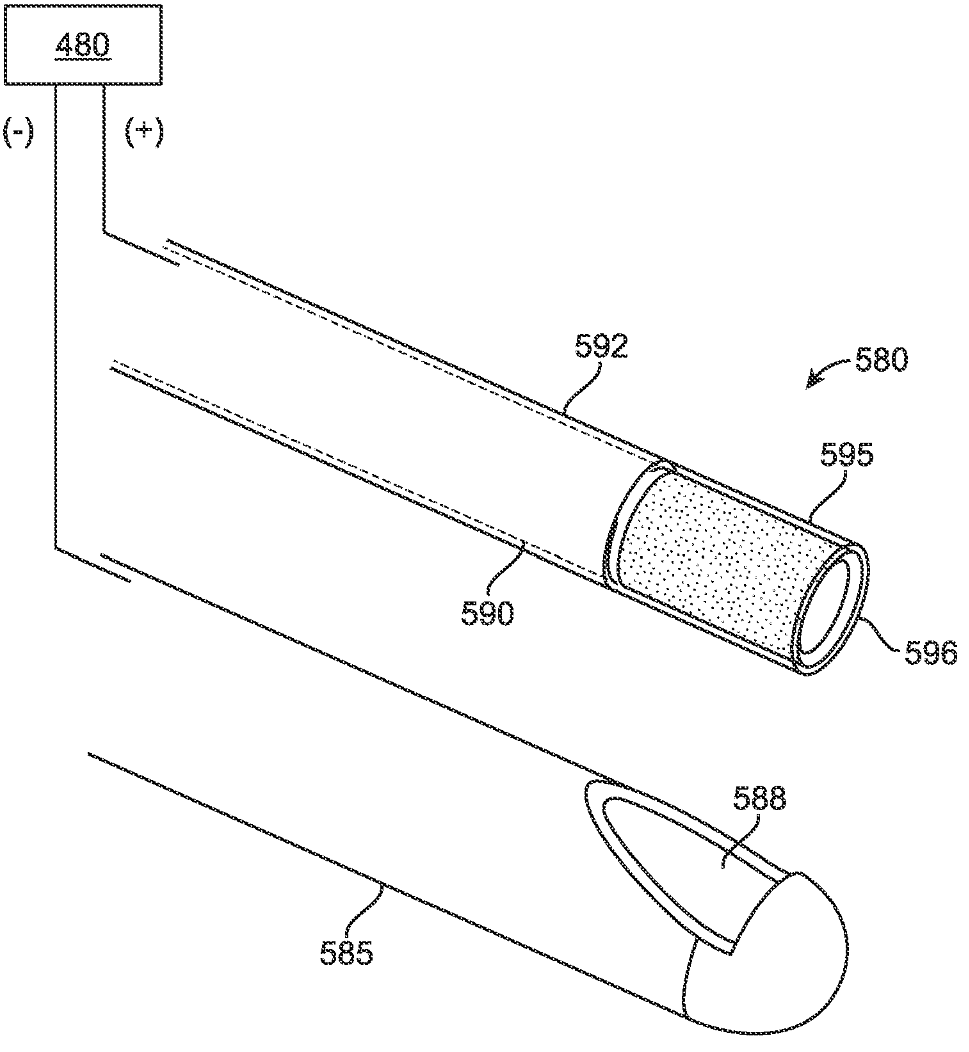
FIG. 17 is a perspective view of a working end of another variation of a probe that shows a reciprocating inner sleeve with a ceramic or glass cutting edge surrounding an electrode sleeve that reciprocates in a metal outer sleeve.

FIG. 17 illustrates another variation of working end 580 that again is similar to that of FIGS. 14 and 15. In this variation, the outer sleeve 585 comprises a thin wall conductive metal with window 588 therein. The inner sleeve 590 comprises a metal sleeve encased in an insulative polymer 592 and a distal ceramic or glass portion 595 that functions as an electrical insulator as well as providing a cutting edge 596. In this variation, the inner sleeve 590 again is adapted to reciprocate rather than rotate in the outer sleeve window 588. Again, an RF source 480 is operatively coupled to both the inner and outer sleeves 585 and 590 to allow for electrosurgical cutting. In use, the reciprocation of inner sleeve and thus can resect tissue mechanically or electrosurgically as described above.

Figure 18:
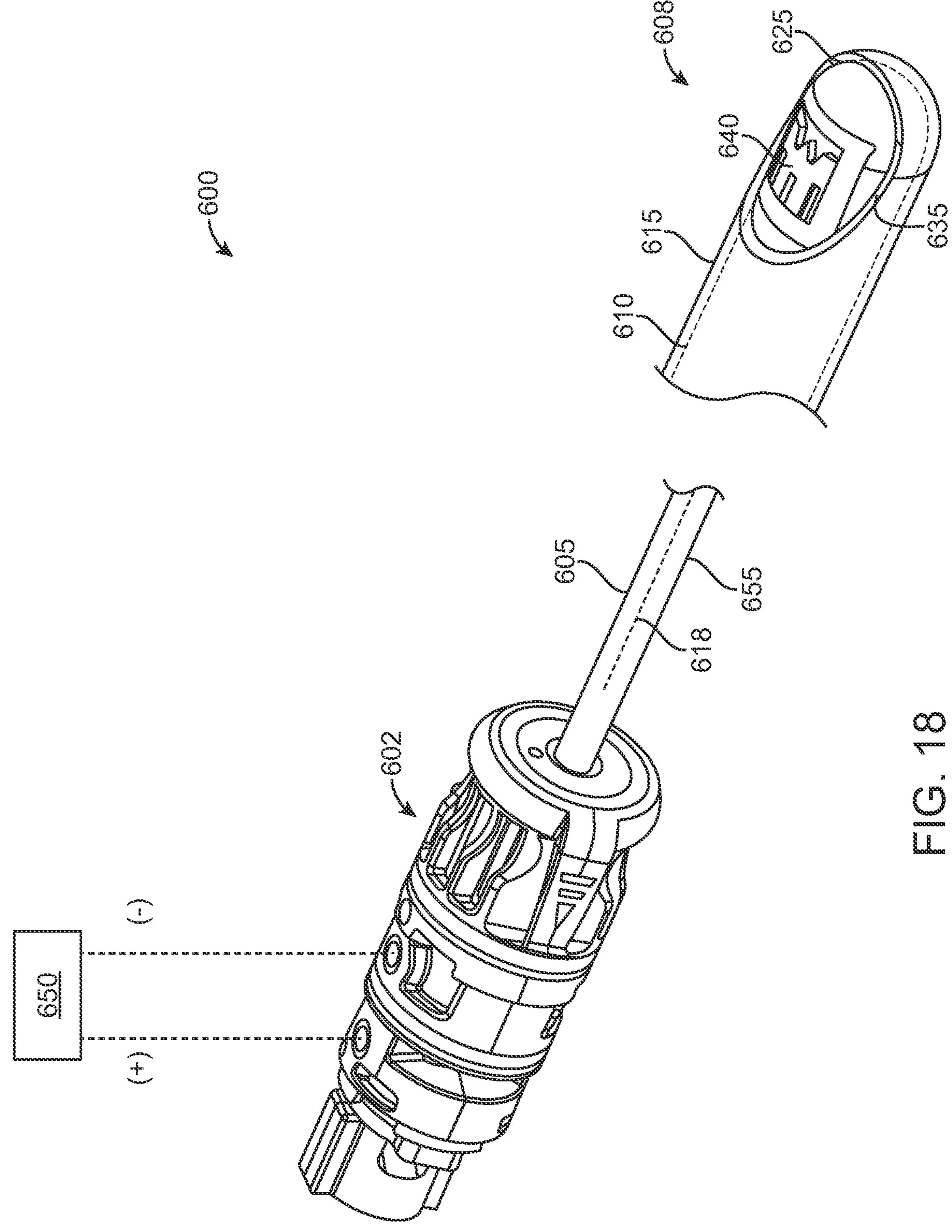
FIG. 18 is a perspective view of another variation of a probe that has a windowed inner sleeve that rotates in a concentric windowed outer sleeve wherein the window edges of both sleeves metal and adapted to cut tissue together with an active electrode carried in a dielectric insert in the inner sleeve.
Figure 19A:
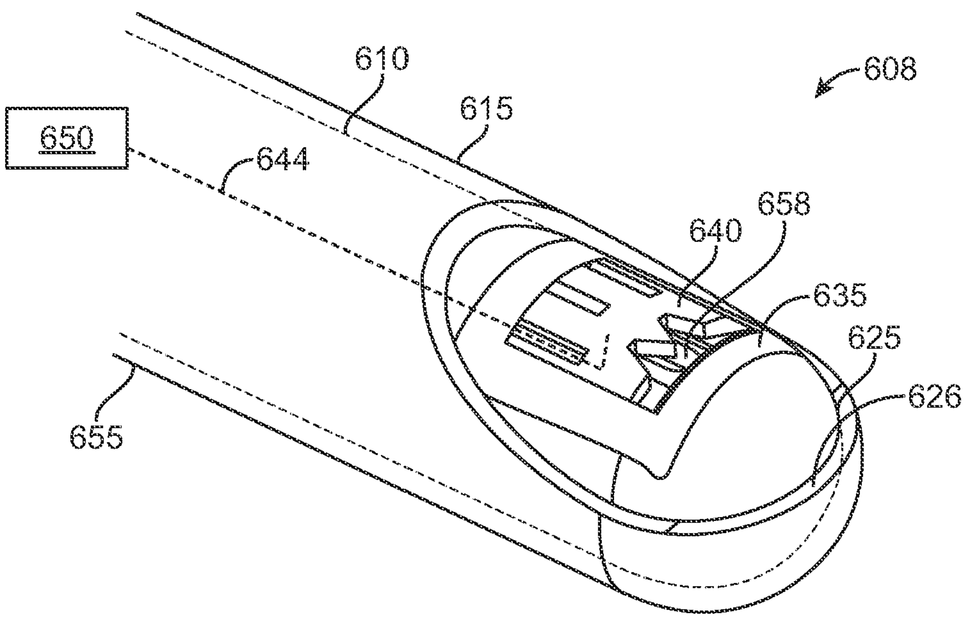
FIG. 19A is an enlarged view of the working end of FIG. 18 in a window-closed position showing the active electrode and the dielectric insert.
Figure 19B:
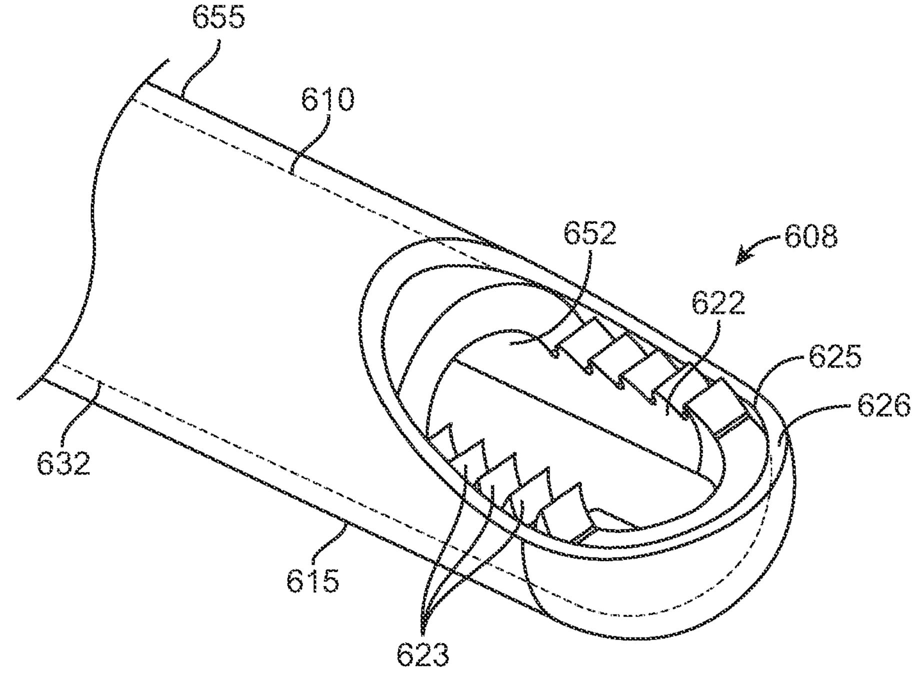
FIG. 19B is a view of the working end of FIG. 19A in a window-open position.

Now turning to FIGS. 18, 19A and 19B, another variation of an arthroscopic shaver or resection probe according to the present invention comprises a tubular cutter 600 having a proximal hub 602 coupled to an elongated shaft assembly 605 having a working end 608 as shown in FIG. 18. The shaft assembly 605 comprises a first or inner sleeve 610 and a second or outer sleeve 615. The sleeves 105 and 110 extend concentrically or coaxially over a longitudinal axis 618 from the hub 602 to the working end 608. The proximal hub 602 may be similar or identical to hubs of the type shown in FIG. 10 and will typically be adapted for coupling to a band piece and motor drive operated by a controller and controller algorithms having the features as described in previous embodiments for rotating the inner sleeve 610 as well as stopping the inner sleeve 610 in a selected rotational position, such as a window-closed position as shown in FIG. 19A or a window-open position as shown in FIG. 19B. The working end 608 has a first or inner sleeve window 622 that rotates in and out of alignment with a second or outer sleeve window 625 for engaging and resecting tissue. In embodiments of FIGS. 18, 19A and 19B, both the inner sleeve 610 and the outer sleeves 615 are electrically conductive, typically being formed in whole or in part of a metal, and are generally configured to provide a working end that is similar to commercially available arthroscopic shavers.

As can be seen in FIGS. 19A and 19B, the elongated shaft assembly 605 and working end 608 differ from previous embodiments herein in that the inner sleeve 610 comprises a thin-wall electrically conductive sleeve 632 having an interior lumen 652, a dielectric insert 635 carrying an active electrode 640 disposed in a wall of the a thin-wall electrically conductive sleeve at or near its distal end. An electrical lead 644 (FIG. 19A) extends from an RF source 650 through the interior lumen 652 of the inner sleeve 610 (FIG. 19B) to the active electrode 640.

In one variation, a return electrode 655 may be formed on or as an integral part of the elongated shaft assembly 605. In some instances, the outer sleeve 615 may be insulated from the inner sleeve 610, and an exposed portion of an exterior surface of the outer sleeve may provide the return electrode, as shown in FIGS. 19A and 19B. In other instances, the inner sleeve 610 and the outer sleeve 615 may be electrically coupled and comprise the return electrode 655.

Referring to FIG. 19A, it can be seen that one or more apertures 658 may be formed adjacent to, or partially underneath, the active electrode 640. Such an aperture 658 is adapted to allow saline flow through the working end 608 of the probe continuously regardless of the rotational orientation of the inner sleeve window 622 relative to the outer sleeve window 625. That is, even when the inner sleeve 610 is rotated so that both the outer sleeve window 625 and the inner sleeve window 622 are be closed, as shown in FIG. 19A, the aperture 658 will allow saline flow into the interior lumen 652 in the inner sleeve 610 when a negative pressure is applied to a proximal end of the interior lumen as described below.

Thus, the probe can be used in a first mode of operation in which the inner sleeve 610 rotates in the outer sleeve 615 to cause the inner sleeve window 622 and outer sleeve window 625 to rotate past each other in order to cut tissue mechanically without the delivery of RF current. Optionally, the inner sleeve window may be configured with cutting teeth or other resection elements 623 formed at least on axially oriented portions of its periphery. Such resection elements may shear against a peripheral surface 626 formed about the periphery of the outer window 625.

In a second mode of operation, the inner sleeve 610 can rotate with the RF source 650 activated to energize the active electrode 640 to enhance tissue cutting. That is, the mechanical shearing of tissue caused by rotation of the inner and outer windows 622 and 625 will continue and be enhanced by the application of RF tissue, typically application of a cutting or ablation current. In other instances, an RF coagulation current might be applied through the electrode 640 while rotating the inner and outer windows 622 and 625 in order to provide simultaneous mechanical resection and electrosurgical coagulation.

In a third mode of operation, the controller and a controller algorithm can be used to stop the rotation of the inner sleeve 610 in the window-closed position of FIG. 19A, and the electrode 640 can be activated to coagulate or ablate tissue without simultaneous mechanical shearing. Tissue ablation can be effected by applying an RF cutting or ablation current and coagulation can be effected by applying an RF coagulation current.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic cutting system, comprising:

a cutting probe, comprising:

a proximal hub;

a metal outer sleeve extending distally from the proximal hub to a working end of the cutting probe, the metal outer sleeve including a proximal end fixedly attached to the proximal hub, the metal outer sleeve further including an outer cutting window formed in a first distal side of the metal outer sleeve, the outer cutting window communicating with an axial bore in the metal outer sleeve that extends proximally from the outer cutting window back through the metal outer sleeve, the outer cutting window including a first sharp metal cutting edge extending around at least part of the outer cutting window;

a metal inner sleeve extending distally from the proximal hub to the working end of the cutting probe and being rotatably received in the axial bore in the metal outer sleeve, the metal inner sleeve including a distal metal portion with an inner cutting window formed therein, the inner cutting window including a second sharp metal cutting edge extending around at least part of the inner cutting window, the metal inner sleeve rotatable in the axial bore in the metal outer sleeve for moving the second sharp metal cutting edge past the first sharp metal cutting edge for resecting tissue at the working end of the cutting probe, the inner cutting window communicating with an axial extraction channel in the metal inner sleeve that extends proximally from the inner cutting window back through the metal inner sleeve for connecting to a negative pressure source;

a dielectric insert carried by the distal metal portion of the metal inner sleeve, wherein, in a longitudinal direction along the metal inner sleeve, a distal end of the dielectric insert extends distally beyond a proximal end of the inner cutting window, and wherein the dielectric insert is circumferentially spaced apart from the inner cutting window around an outer surface of the metal inner sleeve; and an active electrode carried by the dielectric insert so as to be at least partly exposed along an outer surface of the dielectric insert, the active electrode also circumferentially spaced apart from the inner cutting window around the outer surface of the metal inner sleeve such that the inner cutting window and the active electrode are alternately rotatable into alignment with the outer cutting window as the metal inner sleeve is rotated in the axial bore in the metal outer sleeve, wherein the metal outer sleeve and the metal inner sleeve are each formed entirely of metal, the metal outer sleeve and the metal inner sleeve being electrically coupled within the cutting probe to form a combined return electrode providing an electrically-conductive pathway extending from the working end of the cutting probe back to the proximal hub.

2. The arthroscopic cutting system of claim 1, wherein the dielectric insert is disposed in a wall of the distal metal portion of the metal inner sleeve.

3. The arthroscopic cutting system of claim 2, wherein the active electrode includes a curved outer surface that conforms to an outer curvature of the wall of the distal metal portion in which the dielectric insert is disposed.

4. The arthroscopic cutting system of claim 1, wherein, along the outer surface of the metal inner sleeve at the working end of the cutting probe, the dielectric insert is fully surrounded by metal of the distal metal portion.

5. The arthroscopic cutting system of claim 4, wherein, along the outer surface of the metal inner sleeve at the working end of the cutting probe, the active electrode is fully surrounded by the dielectric insert to electrically isolate the active electrode from the distal metal portion of the metal inner sleeve.

6. The arthroscopic cutting system of claim 5 further comprising a radiofrequency (RF) power supply configured to be coupled to the active electrode and the return electrode.

7. The arthroscopic cutting system of claim 6, wherein the controller is configured to operate the motor drive unit and the RF power supply in each of:

a first mode for mechanical tissue cutting wherein the motor drive is activated to move the second sharp metal cutting edge past the first sharp metal cutting edge for resecting tissue at the working end of the cutting probe and the RF power supply is not activated;

a second mode for a combination of mechanical and electrosurgical tissue cutting wherein the motor drive is activated to move the second sharp metal cutting edge past the first sharp metal cutting edge for resecting tissue at the working end of the cutting probe and the RF power supply is activated to deliver a cutting, ablation, or coagulation current to the active electrode; and a third mode where the motor drive positions the active electrode in the outer cutting window and the RF power supply is activated to deliver a cutting current, ablation current, or coagulation current to the active electrode.

8. The arthroscopic cutting system of claim 7 further comprising a negative pressure source configured to be coupled to the axial extraction channel of the metal inner sleeve.

9. The arthroscopic cutting system of claim 8, wherein the controller is configured to operate the negative pressure source.

10. The arthroscopic cutting system of claim 1, wherein part of the distal metal portion extends distally past the dielectric insert along the outer surface of the metal inner sleeve.

11. The arthroscopic cutting system of claim 1, wherein the distal metal portion forms a distal-most tip of the metal inner sleeve.

12. The arthroscopic cutting system of claim 1 further comprising a handpiece configured to removably connect to the proximal hub and including a motor drive unit with a rotatable motor shaft, wherein the metal inner sleeve is coupled to a drive coupling in the proximal hub, the drive coupling couplable to the rotatable motor shaft for rotating the metal inner sleeve relative to the outer sleeve.

13. The arthroscopic cutting system of claim 12 further comprising a controller adapted to selectively drive the motor drive unit for selectively positioning the active electrode in the outer cutting window.

14. The arthroscopic cutting system of claim 1, wherein the active electrode is circumscribed by the dielectric insert which electrically isolates the active electrode from the distal metal portion of the metal inner sleeve.

15. The arthroscopic cutting system of claim 1, wherein an aperture extends through the active electrode and the dielectric insert.

16. The arthroscopic cutting system of claim 15, wherein the metal inner sleeve is sealed at a distal end thereof except for the inner cutting window and the aperture such that a negative pressure applied to a proximal end of the axial extraction channel can aspirate through either the inner cutting window or the aperture.

17. The arthroscopic cutting system of claim 1, wherein the active electrode and dielectric insert are disposed on a side of the metal inner sleeve opposite the inner cutting window.

18. The arthroscopic cutting system of claim 1, wherein a distal end of the outer sleeve is bullet-shaped with the outer cutting window formed thereacross.

19. The arthroscopic cutting system of claim 1, wherein a distal end on the metal inner sleeve is bullet-shaped with the inner cutting window formed thereacross.

20. The arthroscopic cutting system of claim 1, wherein the inner cutting window nests in the outer cutting window when aligned with the outer cutting window.

* * * * *